(12) United States Patent
Singh et al.

(10) Patent No.: US 12,378,223 B2
(45) Date of Patent: Aug. 5, 2025

(54) PROCESS FOR PREPARATION OF TRIAMINOPYRIMIDINE COMPOUND AND INTERMEDIATES THEREOF

(71) Applicant: Zydus Lifesciences Limited, Gandhinagar (IN)

(72) Inventors: Kumar Kamlesh Singh, Gandhinagar (IN); Nikhil Amar Singh, Gandhinagar (IN); Ganapatdan Shimbhu Charan, Gandhinagar (IN); Nimeshkumar Mukeshkumar Shah, Gandhinagar (IN); Sunil Dnyaneshwar Narode, Gandhinagar (IN); Dipakkumar Dhanjibhai Vachhani, Gandhinagar (IN); Amol Kashinath Patil, Gandhinagar (IN); Sandip Pundlik Khairnar, Gandhinagar (IN)

(73) Assignee: ZYDUS LIFESCIENCES LIMITED, Gandhinagar (IN)

( * ) Notice: Subject to any disclaimer, the term of this patent is extended or adjusted under 35 U.S.C. 154(b) by 1569 days.

(21) Appl. No.: 16/640,491

(22) PCT Filed: Sep. 4, 2018

(86) PCT No.: PCT/IB2018/056732
§ 371 (c)(1),
(2) Date: Feb. 20, 2020

(87) PCT Pub. No.: WO2019/049021
PCT Pub. Date: Mar. 14, 2019

(65) Prior Publication Data
US 2020/0207738 A1   Jul. 2, 2020

(30) Foreign Application Priority Data

Sep. 5, 2017  (IN) .............................. 201721031453
Sep. 27, 2017 (IN) .............................. 201721034342

(51) Int. Cl.
C07D 401/14 (2006.01)
A61P 33/06 (2006.01)
C07D 213/73 (2006.01)

(52) U.S. Cl.
CPC ........ C07D 401/14 (2013.01); *C07B 2200/13* (2013.01)

(58) Field of Classification Search
CPC ................ C07D 401/14; C07D 213/73; C07B 2200/13; Y02A 50/30; A61P 33/06
See application file for complete search history.

(56) References Cited

FOREIGN PATENT DOCUMENTS

WO   WO-2015165660 A1 * 11/2015   .......... A61K 31/506

OTHER PUBLICATIONS

Ermrich et al., XRD for the analyst: Getting acquainted with the principles, published by PANalytical GmBH, ISBN: 978-90-809086-0-4, pp. 1-92 (Year: 2011).*

(Continued)

*Primary Examiner* — Jeffrey S Lundgren
*Assistant Examiner* — Alexander K. Showalter
(74) *Attorney, Agent, or Firm* — Nixon & Vanderhye, PC

(57) ABSTRACT

The present invention relates to triaminopyrimidine compound 1, or pharmaceutically acceptable salts thereof, or hydrates, or solvates, or polymorphs, or optically active forms thereof, in solid state forms. The invention also relates to a process for preparation of triaminopyrimidine compound and intermediates thereof. The present invention also relates to a pharmaceutical composition comprising pure triaminopyrimidine compound, useful for preventing or treating malaria.

(Continued)

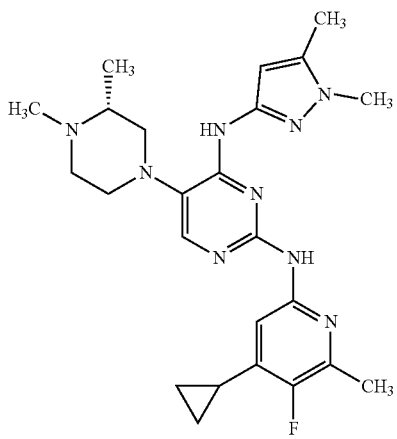

25 Claims, 7 Drawing Sheets

(56) References Cited

OTHER PUBLICATIONS

Hameed P. et al., Triaminopyrimidine is a fast-killing and long-acting antimalarial clinical candidate, Nat. Comm., 6, article No. 6715, pp. 1-11 (Year: 2015).*

Ramachandran et al., N-Aryl-2-aminobenzimidazoles: Novel, Efficacious, Antimalarial Lead Compounds, J. Med. Chem, 57, pp. 6642-6652 (Year: 2014).*
Bernstein, "Analytical techniques for studying and characterizing polymorphs and polymorphic transitions" Polymorphism in Molecular Crystals, 2nd edition, Editor Bernstein, Oxford Univ. Press, pp. 136-214 (Year: 2020).*
Reed et al., Purification of veratridine from veratrine using high-performance liquid chromatography, J. Chromatog., 356, pp. 450-454 (Year: 1986).*
Bhattacharya et al., "Thermoanalytical and Crystallographic Methods." Polymorphism in Pharmaceutical Solids, 2nd edition, Editor Brittain, Publ. Informa Healthcare USA, pp. 318-346 (Year: 2009).*
Cruz-Cabeza et al., Open questions in organic crystal polymorphism, Commun. Chem., 3, art. No. 142, pp. 1-4 (Year: 2020).*
Price, Why don't we find more polymorphs?, Acta. Cryst. B, 69, pp. 313-328 (Year: 2013).*
Shahul Hameed P., et al.; Triaminopyrimidine is a fast-killing and long-acting antimalarial clinical candidate; Published Mar. 31, 2015; Nature Communications; www.nature.com/naturecommunications; 11 Pages.
Monica A. Fitzgerald, et al.; Ni-Catalyzed C—H Functionalization in the Formation of a Complex Heterocycle, the Synthesis of the Potent JAK2 Inhibitor, BMS-911543; The Journal of Organic Chemistry; http://pubs.acs.org; Apr. 7, 2015; 33 Pages.
Mino R. Caira; Crystalline Polymorphism of Organic Compounds; Department of Chemistry, University of Cape Town, Topics in Current Chemistry, vol. 198, 46 Pages; Jan. 1998.

* cited by examiner

PROCESS FOR PREPARATION OF TRIAMINOPYRIMIDINE COMPOUND AND INTERMEDIATES THEREOF

FIELD OF THE INVENTION

The present invention relates to a process for preparation of triaminopyrimidine compound and intermediates thereof. In particular, the present invention relates to a process for preparing pure triaminopyrimidine compound. The present invention also relates to a pharmaceutical composition comprising pure triaminopyrimidine compound, useful for preventing or treating malaria.

BACKGROUND OF THE INVENTION

The following discussion of the prior art is intended to present the invention in an appropriate technical context and allow its significance to be properly appreciated. Unless clearly indicated to the contrary, however, reference to any prior art in this specification should be construed as an admission that such art is widely known or forms part of common general knowledge in the field.

Malaria is caused by protozoan parasites of the genus *Plasmodium* that infect and destroy red blood cells, leading to fever, severe anemia, cerebral malaria and, if untreated, death.

International (PCT) Publication No. WO 2015/165660 (the WO '660) discloses triaminopyrimidine compounds, intermediates, pharmaceutical compositions and methods for use for preventing or treating malaria. The WO '660 discloses a process for preparation of 4-cyclopropyl-5-fluoro-6-methylpyridin-2-amine (compound 5) as depicted in scheme-1.

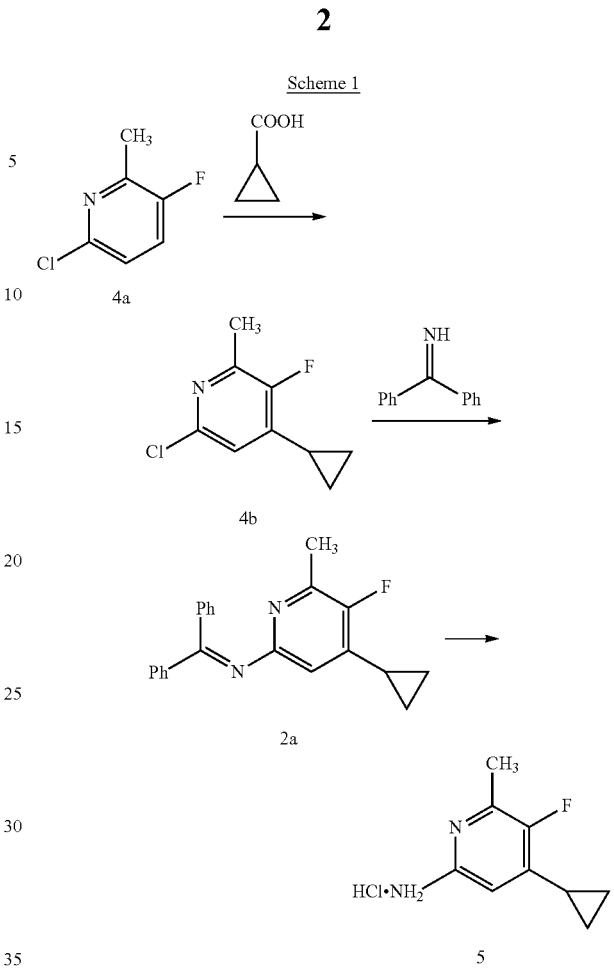

WO '660 discloses a process for preparation of triaminopyrimidine compounds as depicted in scheme-2.

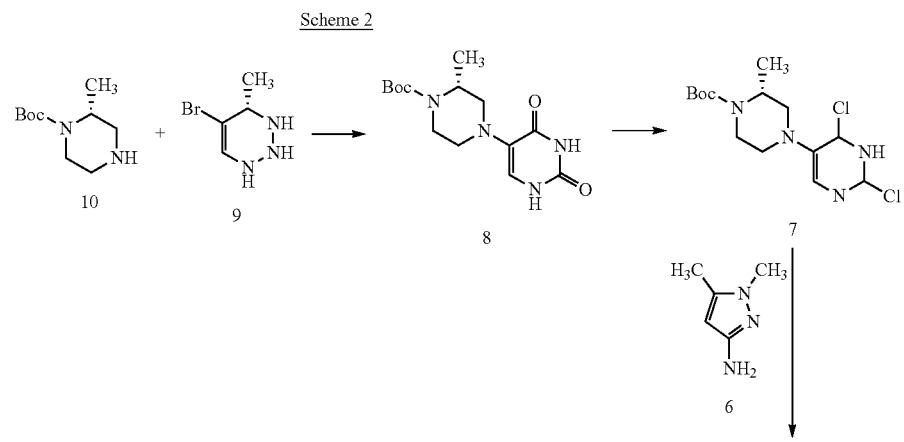

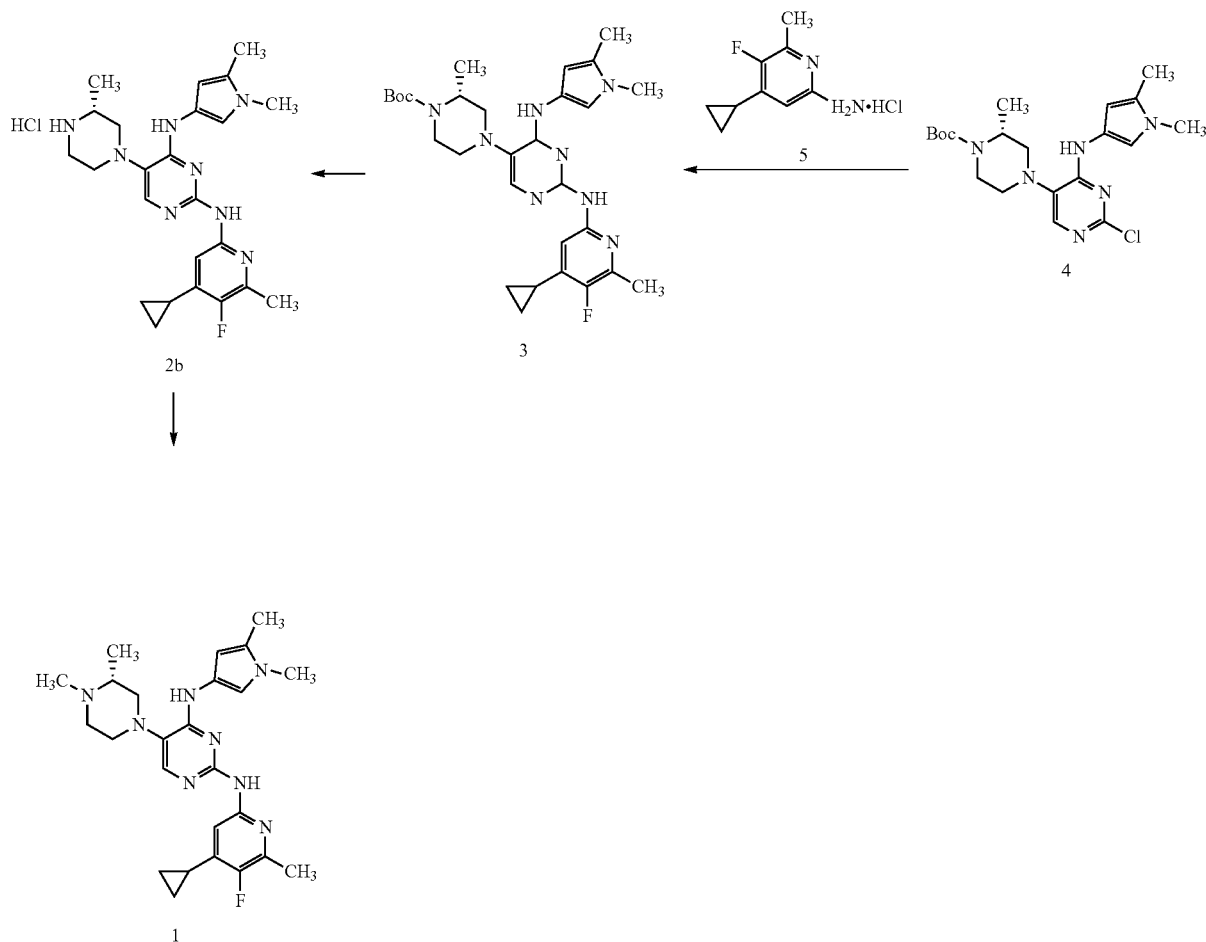

WO '660 discloses the preparation of compounds 8 and 4 by using microwave technique using Biotage microwave vial. WO '660 in example-13, discloses the isolation of compound 1 by concentration of reaction mixture to obtain crude product, which was purified through reverse phase HPLC GILSON instrument to obtain pure solid compound 1 in 40.8% yield, without providing the purity of the solid compound 1. The process disclosed in WO '660 is not industrially advantageous as it requires microwave conditions as well as chromatographic purification and provides compound 1 with lower yields. The compound 1 prepared may not be suitable for pharmaceutical preparations based on various regulatory requirements.

Polymorphism, the occurrence of different crystalline forms, is a property of some molecules. A single molecule can exist in different crystalline forms having distinct physical properties like melting point, thermal behaviors (e.g. measured by thermogravimetric analysis—TGA, or different scanning calorimetry—DSC, Powder x-ray diffraction pattern—PXRD, infrared absorption—IR). One or more these techniques may be used to distinguish different polymorphic forms of a compound.

Different salts and solid states (e.g. solvates, hydrates) of an active pharmaceutical ingredient may possess different physio-chemical properties. Such variation in the properties of different salts and solid states forms may provide a basis for improving formulation, for example, by facilitating better processing or handling characteristics, changing the dissolution profile in a favorable direction, or improving stability (both chemical and polymorph) and shelf-life. These variations in the properties of different salts and solid states forms may offer improvements to the final dosage form for example, to improve bioavailability. Different salts and solid state forms of an active pharmaceutical ingredient may also give rise to a variety of polymorphs or crystalline forms or amorphous form, which may in turn provide additional opportunities to assess variations in the properties and characteristics of an active pharmaceutical ingredient.

In view of the above, the present invention provides a process for the preparation of triaminopyrimidine compound 1 or pharmaceutically acceptable salts thereof or hydrates or solvates or polymorphs or optically active forms thereof, which is industrially scalable, environment friendly and efficient so as to obtain compounds of the invention in higher yields and purity.

The process for the preparation of triaminopyrimidine compound 1 or intermediates thereof of the present invention, takes the advantage by using appropriate solvent systems and isolation techniques as well as purification techniques, thereby to overcome problems of lower yields, chromatography purifications and microwave reactions of the prior art.

SUMMARY OF THE INVENTION

The present invention provides solid state forms of triaminopyrimidine compound 1,

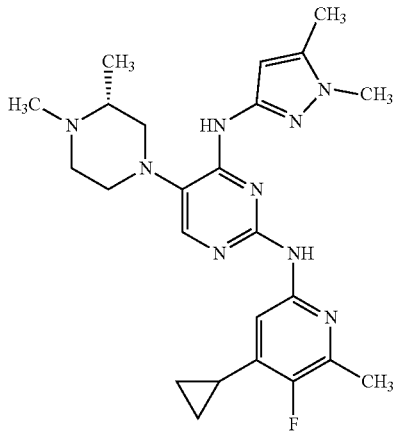

or pharmaceutically acceptable salts thereof, or hydrates, or solvates, or polymorphs, or optically active forms thereof, in solid state forms.

The present invention provides solid state forms of triaminopyrimidine compound 1 or pharmaceutically acceptable salts thereof and use in the preparation of pharmaceutical compositions and/or formulations for use in medicine, preferably for the treatment of malaria.

In one general aspect, the present invention provides pharmaceutical compositions and/or pharmaceutical formulations comprising any one or a combination of the solid forms of triaminopyrimidine compound 1 or pharmaceutically acceptable salts thereof.

In another general aspect, the present invention provides different crystalline forms of triaminopyrimidine compound 1 and intermediates thereof.

In another general aspect, there is provided substantially pure triaminopyrimidine compound 1 having a purity of about 98% or more by weight, of about 99% or more by weigh, of about 99.5% or more by weight, of about 99.8% or more by weight, of about 99.9% or more by weight, by area percentage of HPLC.

In another general aspect, there is provided substantially pure compound 5 or hydrate thereof having a purity of about 99% or more by weight, of about 99.5% or more by weight, of about 99.8% or more by weight, measured by area percentage by HPLC.

In another general aspect, there is provided crystalline compound 5. In general, the crystalline compound 5 is a hydrate. In particular, the crystalline compound 5 is a monohydrate.

In another general aspect, there is provided a process for the preparation of compound 5 or a hydrate thereof,

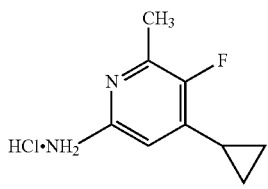

the process comprising:
(a) reacting compound 4a with cyclopropane carboxylic acid in one or more solvents to obtain a compound 3a;

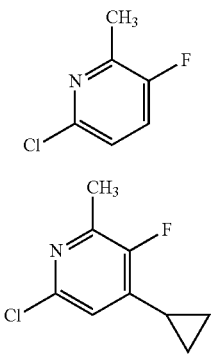

(b) reacting the compound 3a with diphenylmethanimine in one or more solvents to obtain compound 2a;

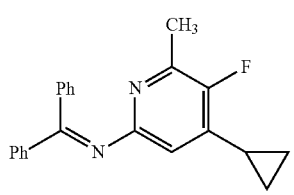

(c) reacting the compound 2a with hydrochloric acid in one or more solvents to obtain the compound 5; and

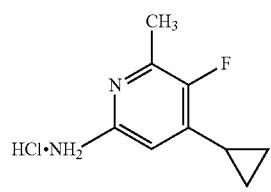

(d) obtaining the compound 5 or a hydrate thereof by crystallizing in one or more solvents.

In another general aspect, there is provided a process for the preparation of compound 6,

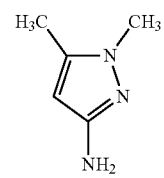

the process comprising:
(a) halogenating 2-butenenitrile to obtain a compound 2,3-dihalobutanenitrile; and
(b) reacting the compound 2,3-dihalobutanenitrile with methyl hydrazine or salts thereof in the presence of a base to obtain compound 6.

In another general aspect, there is provided a process for the preparation of triaminopyrimidine compound 1, the process comprising:

(a) reacting compound 10 with compound 9 in one or more solvents to obtain compound 8;

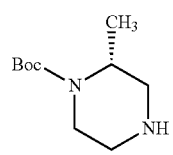
10

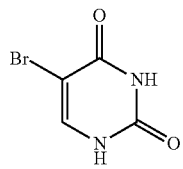
9

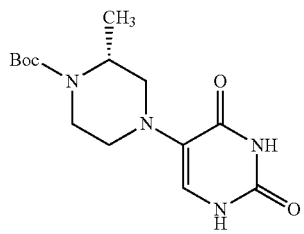
8

(b) reacting the compound 8 with a chlorinating agent in one or more solvents to obtain compound 7;

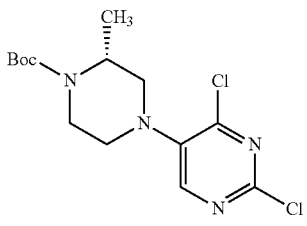
7

(c) reacting the compound 7 with compound 6 in one or more solvents in the presence of a base to obtain compound 4;

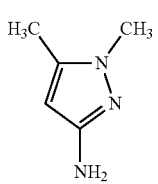
6

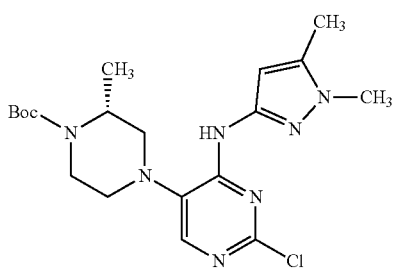
4

(d) reacting the compound 4 with compound 5 or a hydrate thereof in one or more solvents in the presence of a base to obtain compound 3;

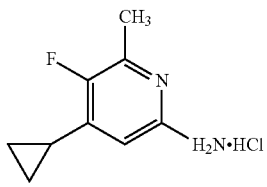
5

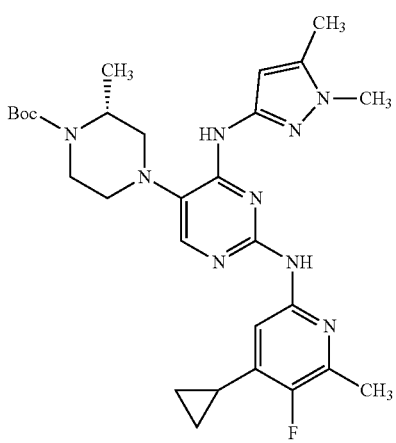
3

(e) reacting the compound 3 or solution thereof with an acid in one or more solvents to obtain compound 2 free base;

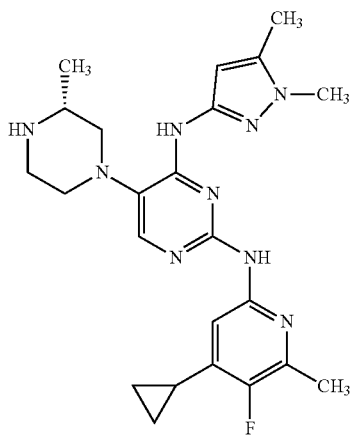
2

(f) reacting the compound 2 free base with a methylating agent in one or more solvents to obtain the compound 1; and (g) optionally, crystallizing the compound 1 in one or more solvents.

In another general aspect, there is provided a free base compound 2, which is an intermediate for the preparation of triaminopyrimidine compound 1,

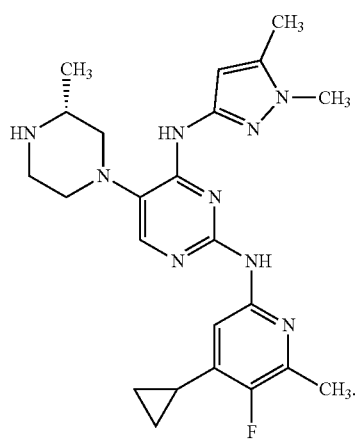

In another general aspect, there is provided a pharmaceutical composition comprising crystalline triaminopyrimidine compound 1, and pharmaceutically acceptable carrier, diluents and excipients.

In another general aspect, there is provided a pharmaceutical composition comprising substantially pure triaminopyrimidine compound 1, and one or more of pharmaceutically acceptable carrier, diluents and excipients.

DETAILED DESCRIPTION OF THE INVENTION

Figure 1:
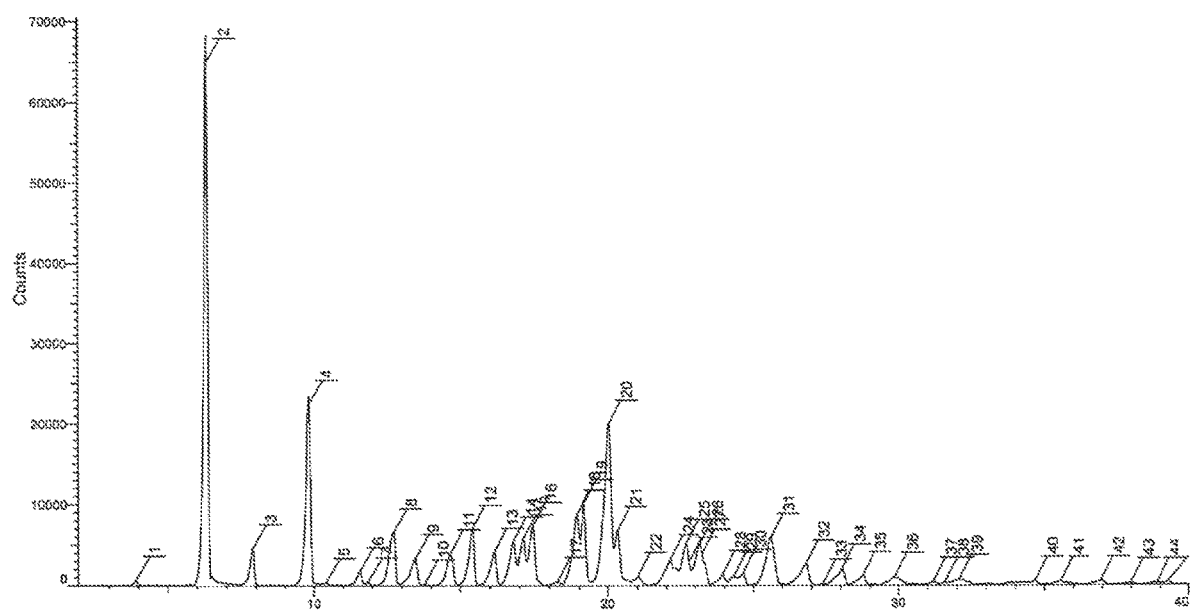
FIG. 1: X-ray powder diffraction pattern of crystalline compound 1 (Ex-16)

The above and other objects of the present invention are achieved by the process of the present invention, which leads a process for the preparation of pure triaminopyrimidine compound 1 in crystalline form and hydrate form of compound 5 in one or more solvents.

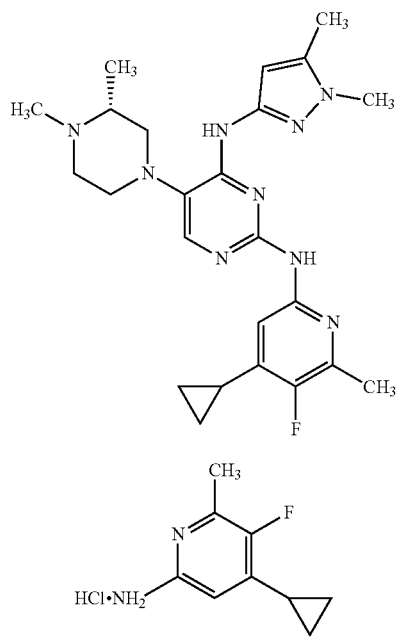

Optionally, the solution, prior to any solids formation, can be filtered to remove any undissolved solids or solid impurities prior to removal of the solvent. Any filtration system and filtration techniques known in the art can be used.

All ranges recited herein include the endpoints, including those that recite a range "between" two values. Term "substantially" is to be construed as modifying a term or value such that it is not an absolute. This includes, at very least, the degree of expected experimental error, technique error and instrument error for a given technique used to measure a value.

The term "substantially pure" means a compound having a purity of at least about 98% or more, by area percentage of HPLC. In particular, the compound is having a purity of at least about 99% or more, more particularly, a purity of at least about 99.5% or more, further more particularly, a purity of at least about 99.8% or more, most particularly, a purity of at least about 99.9% or more by area percentage of HPLC.

The term "substantially free" means triaminopyrimidine compound 1 having one or more each of compound 11, compound 12, compound 13, compound 14, compound 15 or other such compounds, of about 1% or less by area percentage of HPLC. In particular, the triaminopyrimidine compound 1 is having one or more each of these compounds, of about 0.5% or less, of about 0.25% or less, of about 0.20% or less, of about 0.15% or less, of about 0.10% or less, of about 0.05% or less, or of about not in detectable amount by an area percentage of HPLC.

As used herein the terms, "treating", "reacting", or "condensing" have meanings as widely used by general prior art in the field of invention and can be easily understood by those skilled in the art.

As used herein the terms, "obtaining", or "getting" may include filtration, filtration under vacuum, centrifugation, and decantation for isolation of the product. The product obtained may be further or additionally dried to achieve the desired moisture values. For example, the product may be dried in a tray drier, dried under vacuum and/or in a Fluid Bed Drier. The product may be preceded for further reaction with or without isolation and with or without drying in case of the product was isolated.

As used herein, the term "solution" or "reaction mixture" does not limit to a clear solution only and includes any hazy or opaque mass obtained.

The term "composition" used herein means a physical mixture of two or more components.

The term "pharmaceutically acceptable" means that which is useful in preparing a pharmaceutical composition that is generally non-toxic and is not biologically undesirable, and includes that which is acceptable for veterinary use and/or human pharmaceutical use.

The term "pharmaceutical composition" is intended to encompass a drug product including the active ingredient(s), pharmaceutically acceptable excipients that make up the carrier, as well as any product which results, directly or indirectly, from combination, complexation or aggregation of any two or more of the ingredients. Accordingly, the pharmaceutical compositions encompass any composition made by admixing the active ingredient, active ingredient dispersion or composite, additional active ingredient(s), and pharmaceutically acceptable excipients.

The term "pharmaceutically acceptable salts" as used herein includes but not limited to acetate, benzenesulfonate, benzoate, bicarbonate, bisulfate, bitartrate, borate, bromide, calcium edetate, camsylate, carbonate, chloride, clavulanate, citrate, dihydrochloride, edetate, edislyate, estolate, esylate, ethylsuccinate, fumarate, gluceptate, gluconate, glutamate, glycolylarsanilate, hexylresorcinate, hydrabamine, hydrobromide, hydrochloride, iodide, isothionate, lactate, lactobionate, laurate, malate, maleate, mandelate, mesylate, methylsulfate, mucate, napsylate, nitrate, oleate, oxalate, pamoate (embonate), palmitate, pantothenate, phospate/diphosphate, polygalacturonate, salicylate, stearate, subacetate, succinate, tannate, tartrate, teoclate, tosylate, triethiodode, and valerate.

As used herein the term "crystallizing" refers to a process comprising: heating a mixture of a starting material and a solvent to a temperature of between about 10° C. below and above the reflux temperature of the solvent to obtain a solution, and cooling the solution to a temperature of about 0° C. to about 35° C.

The terms used throughout the description is defined herein below.

"BINAP" refers to 2,2'-bis-(diphenylphosphino)-1,1'-binaphthyl

"TEA" refers to Triethylamine

"DIPEA" refers to N,N-Diisopropylethylamine

"STB" refers to Sodium-tert-butoxide

"PTB" refers to Potassium-tert-butoxide

"Xantphos" refers to 4,5-Bis-(diphenylphosphino)-9,9-dimethylxanthene

"XPhos" refers to 2-Dicyclohexylphosphino-2',4',6'-triisopropylbiphenyl

"DBU" refers to 1,8-Diazabicyclo-(5.4.0)-undec-7-ene

"DABCO" refers to 1,4-Diazabicyclo-[2.2.0]-octane

In one general aspect, there is provided a triaminopyrimidine compound 1,

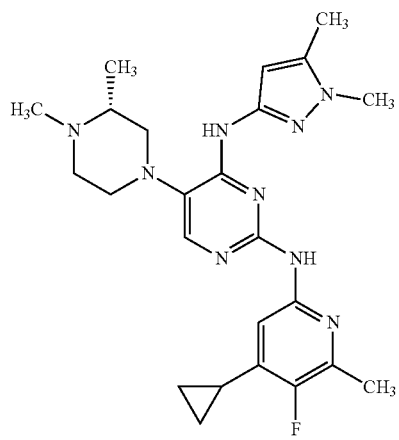

or pharmaceutically acceptable salts thereof, or hydrates, or solvates, or polymorphs, or optically active forms thereof, in solid state forms.

In another general aspect, the present invention disclosure provides different crystalline forms of triaminopyrimidine compound 1, or intermediates thereof.

In general, the present invention provides crystalline forms of triaminopyrimidine compound 1. The crystalline forms of triaminopyrimidine compound 1 are represented hereinafter as "Form I" and "Form II".

In general, the present invention provides a crystalline Form I of triaminopyrimidine compound 1. In general, the crystalline Form I triaminopyrimidine compound 1 is characterized by powder x-ray diffraction pattern having peaks expressed in degrees 2θ at 6.3° and 9.8°±0.2 2θ.

In general, the crystalline Form I of the present invention is further characterized by powder x-ray diffraction pattern having peaks expressed in degrees 2θ at 6.3°, 7.8, 9.8°, 15.4°, and 20.0°±0.2 2θ; a differential scanning calorimetry analysis having onset at about 179° C.±5° C. and endothermic peak at about 181° C.±5° C.

Figure 2:
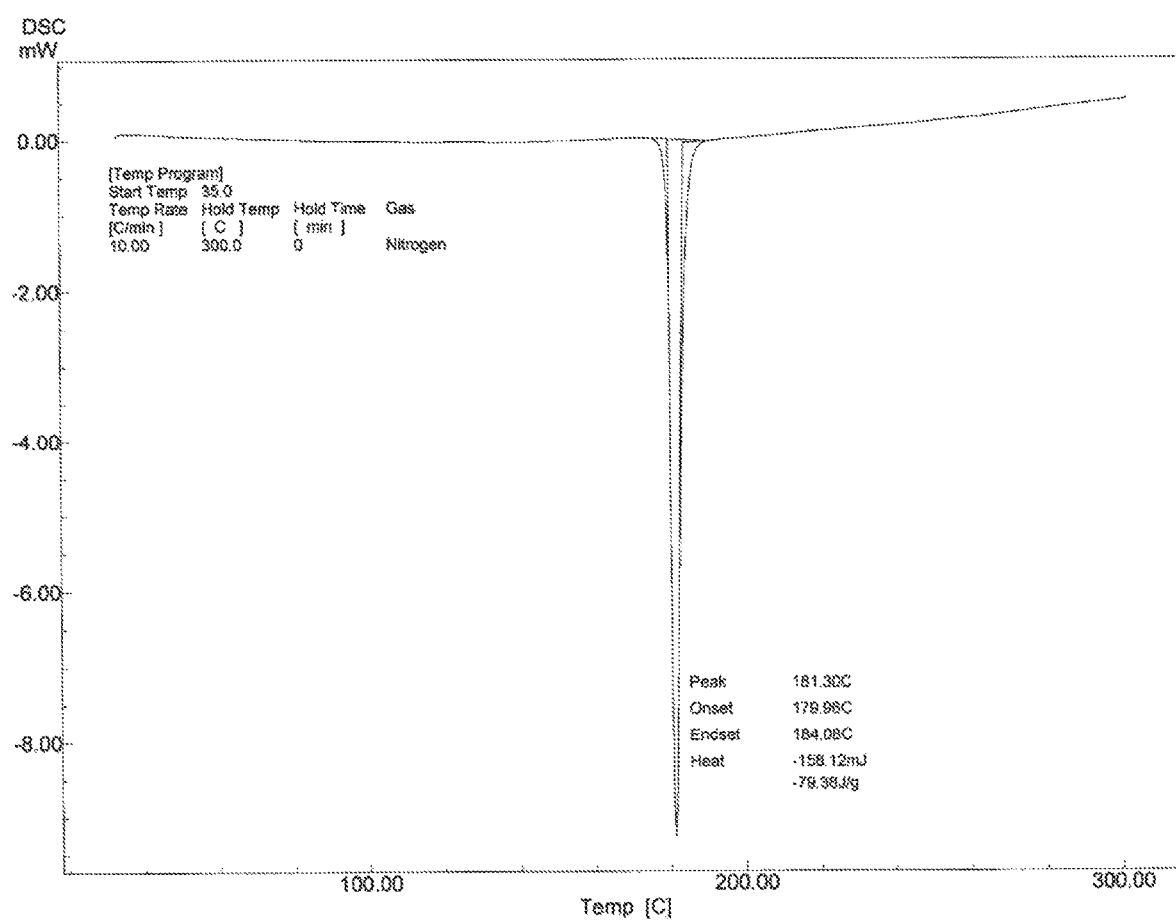
FIG. 2: Differential Scanning Calorimetry of crystalline compound 1 (Ex-16)

In general, the present invention provides crystalline Form I of triaminopyrimidine compound 1 further characterized by powder x-ray diffraction pattern substantially same as depicted in FIG. 1 and differential scanning calorimetry substantially same as depicted in FIG. 2.

In general, the present invention provides crystalline Form II of triaminopyrimidine compound 1. In general, the crystalline Form II of the present invention is characterized by powder x-ray diffraction pattern having peaks expressed in degrees 2θ at 13.8°, 21.9°, and 23.7°±0.2 2θ.

In general, the crystalline Form II of the present invention is further characterized by powder x-ray diffraction pattern having peaks expressed in degrees 2θ at 8.3°, 12.1°, 13.8°, 21.9°, and 23.7°±0.2 2θ; a differential scanning calorimetry analysis having at least one onset at about 161° C.±5° C. and endothermic peak at about 163° C.±5° C.; a differential scanning calorimetry having one onset at about 161° C.±5° C. and second onset at about 179° C.±5° C.; a differential scanning calorimetry having one endothermic peak at about 163° C.±5° C. and second endothermic peak at about 181° C.±5° C.

Figure 3:
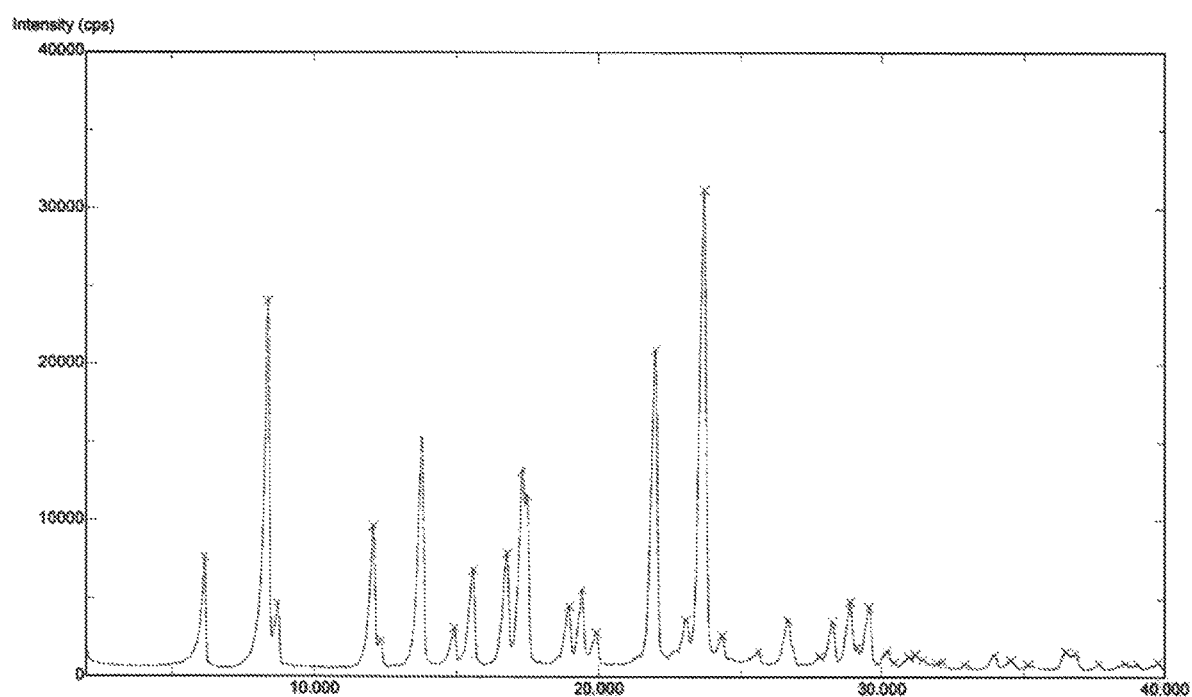
FIG. 3: X-ray powder diffraction pattern of crystalline compound 1 (Ex-17)
Figure 4:
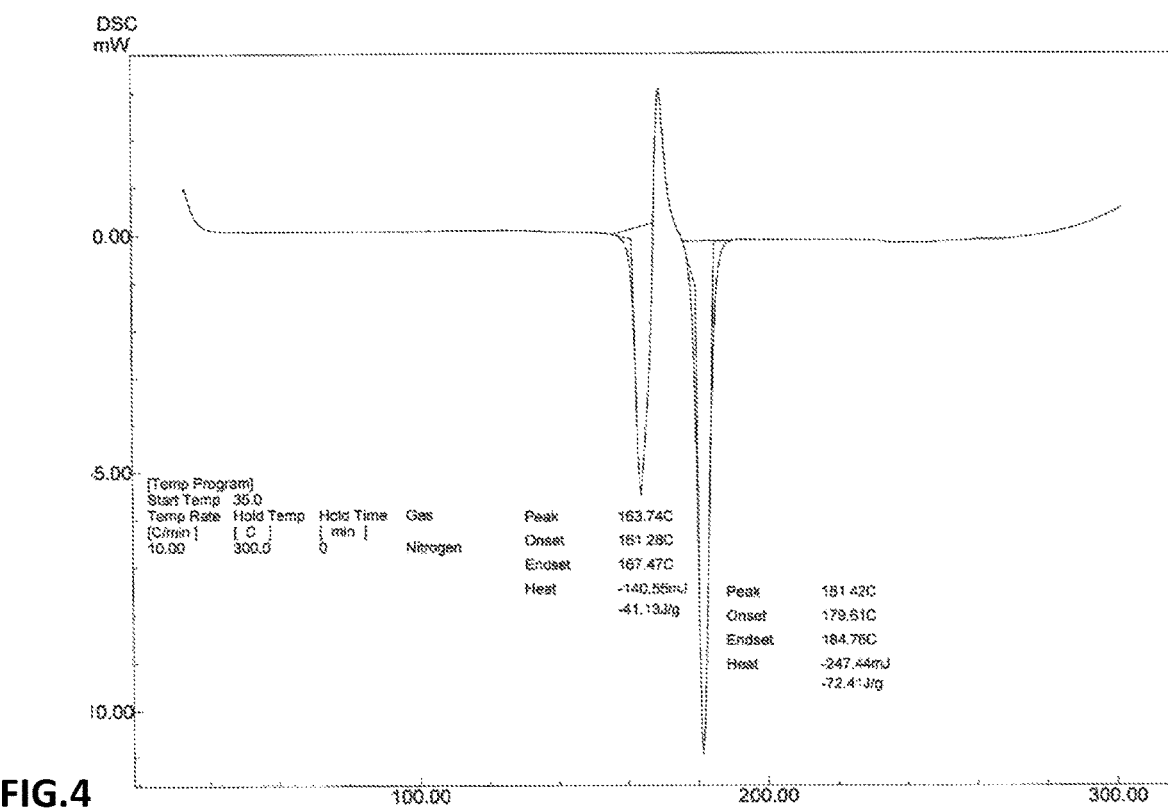
FIG. 4: Differential Scanning Calorimetry of crystalline compound 1 (Ex-17)

In general, the present invention provides crystalline Form II of triaminopyrimidine compound 1 further characterized by powder x-ray diffraction pattern substantially as same as depicted in FIG. 3 and differential scanning calorimetry substantially as same as depicted in FIG. 4.

In another general aspect, there is provided compound 5, or a hydrate thereof,

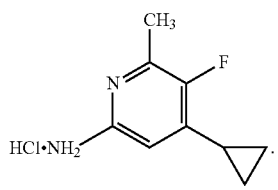

In general, the compound 5 is monohydrate, having water loss of about 8% or more substantially as shown by thermogravimetric analysis.

In another general aspect, there is provided crystalline compound 5. In general, the crystalline compound 5 is a hydrate. In particular, the crystalline compound 5 is monohydrate.

In general, the crystalline compound 5 is further characterized by powder x-ray powder diffraction pattern having peaks expressed in degrees 2θ at 10.5°, 12.7°, and 25.1°±0.2 2θ.

In general, the crystalline compound 5 is further characterized by powder x-ray diffraction pattern having peaks expressed in degrees 2θ at 10.5°, 12.7°, 25.1°, and 25.7°±0.2 2θ; a differential scanning calorimetry analysis having one onset at about 106° C.±5° C. and endothermic peak at about 108° C.±5° C.; a thermogravimetric analysis having water loss of about 8% or more.

Figure 5:
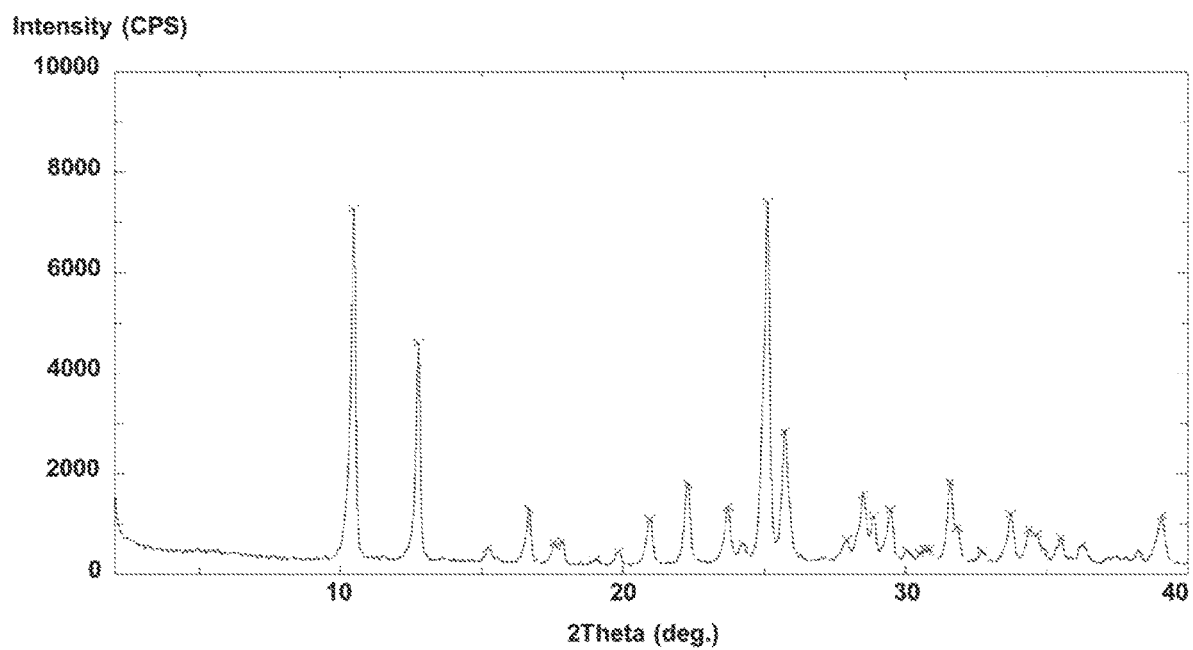
FIG. 5: X-ray powder diffraction pattern of compound 5 (Ex-6)
Figure 6:
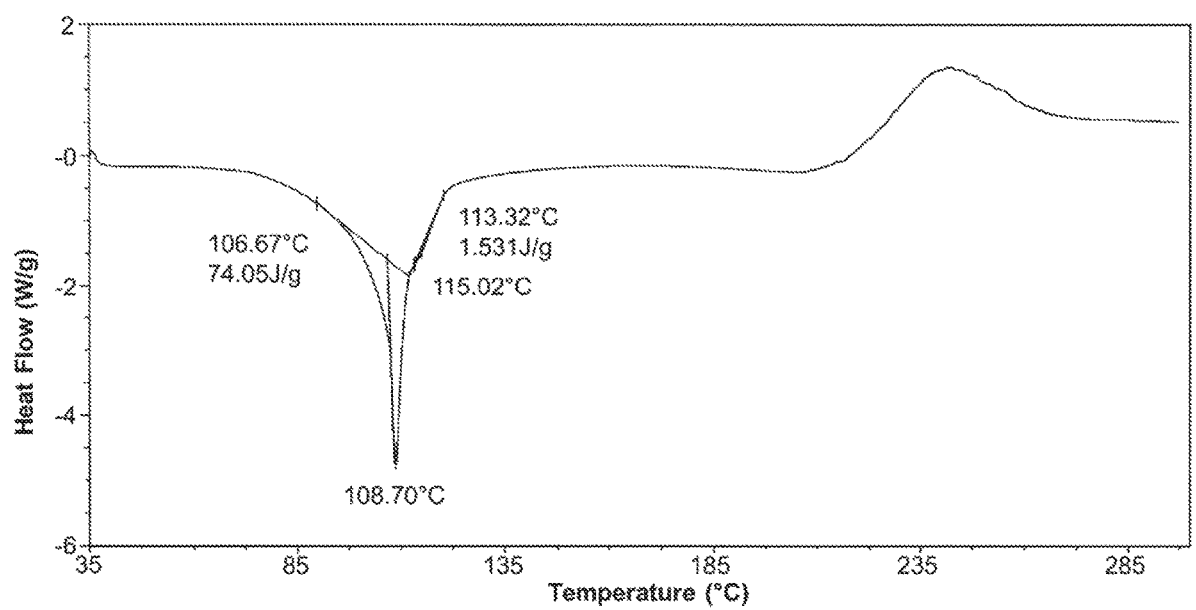
FIG. 6: Differential Scanning Calorimetry of compound 5 (Ex-6)
Figure 7:
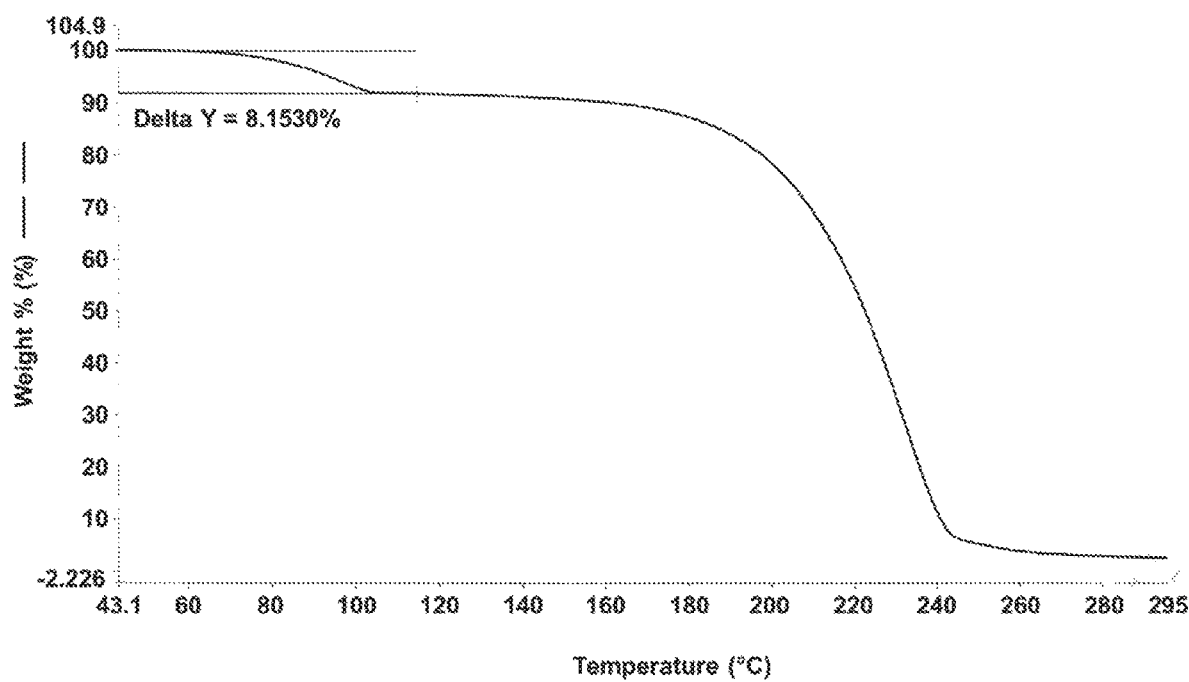
FIG. 7: Thermogravimetric analysis of compound 5 (Ex-6)

In general, the crystalline compound 5 is further characterized by Powder x-ray diffraction pattern substantially same as depicted in FIG. 5, Differential Scanning calorimetry (DSC) substantially same as depicted in FIG. 6 and Thermogravimetric Analysis (TGA) curve substantially same as depicted in FIG. 7.

In another general aspect, there is provided substantially pure compound 5 or hydrate thereof having a purity of about 98% or more, of about 99% or more, of about 99.5% or more, of about 99.8% or more by weight by area percentage by HPLC.

In another general aspect, there is provided substantially pure compound 5 substantially free from one or more of compounds 4b or 4c,

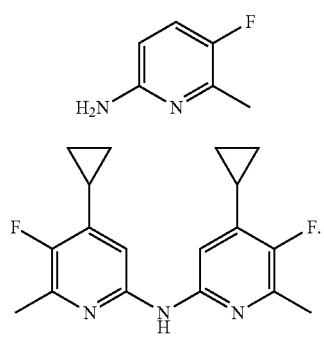

In general, the results of the analysis using HPLC of the compound 5 or hydrate thereof, prepared by the process of the present invention, has total impurities of about 0.5% or less, by weight by area percentage of HPLC and purity of about 99.5% or more, by weight by area percentage of HPLC.

In another general aspect, there is provided compound 5b, which is a free base,

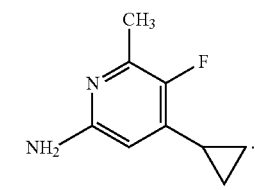

In another general aspect, there is provided a free base compound 2, which is an intermediate for the preparation of triaminopyrimidine compound 1.

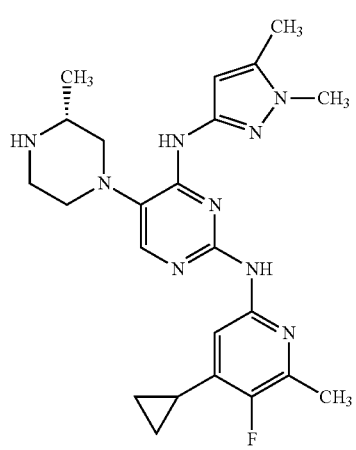

In another general aspect, there is provided a process for the preparation of compound 5, or a hydrate thereof,

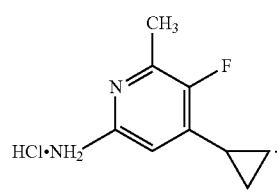

the process comprising:
(a) reacting compound 4a with cyclopropane carboxylic acid in one or more solvents to obtain compound 3a;

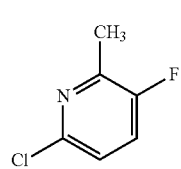

3a

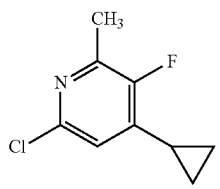

(b) reacting the compound 3a with diphenylmethanimine in one or more solvents to obtain compound 2a;

2a

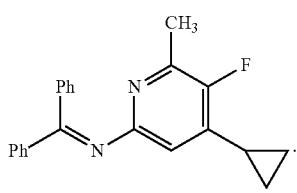

(c) reacting the compound 2a with hydrochloric acid in one or more solvents to obtain the compound 5; and

5

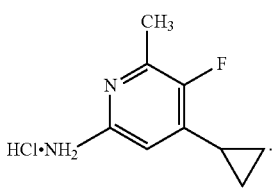

(d) obtaining the compound 5 or a hydrate thereof by crystallizing in one or more solvents.

In general, the hydrate of compound 5 obtained in step (e) is monohydrate.

In another general aspect, there is provided a process for the preparation of compound 5 or hydrate thereof wherein the intermediate compound 3a and 2a are not isolated. The reaction of compound 4 to compound 5 or hydrate thereof may be performed in single solvent in one-pot process.

In general, the compound 4 is reacted with cyclopropanecarboxylic acid to obtain compound 3a in the presence of an acid and an oxidizing agent, optionally in the presence of one or more solvents.

In general, the acid comprises one or more of sulfuric acid, hydrochloric acid, hydrobromic acid, acetic acid, phosphoric acid, and trifluroacetic acid. In particular, sulfuric acid may be used.

The oxidizing agent is selected from the group consisting of mixture of ammonium persulfate and silver nitrate.

In general, the solvent comprises one or more of methanol, ethanol, isopropanol, butanol, acetone, methyl ethyl ketone, methyl isobutyl ketone, ethyl acetate, isopropyl acetate, butyl acetate, methylene dichloride, toluene, xylene, ethylbenzene, dimethylformamide, dimethylacetamide, dimethylsulfoxide, 1,4-dioxane, tetrahydrofuran, acetonitrile and water or mixtures thereof. In particular, the solvent is water.

In general, the compound 3a is reacted with diphenylmethanimine to obtain compound 2a in the presence of a base, a catalyst and a ligand in one or more solvents.

In general, the base comprises one or more of sodium hydroxide, potassium hydroxide, lithium hydroxide, barium hydroxide, sodium carbonate, potassium carbonate, barium carbonate, cesium carbonate, sodium bicarbonate, potassium bicarbonate, STB, PTB, pyridine, piperidine, morpholine, TEA, DIPEA, DBU, or DABCO. In particular, the STB may be used.

In general, the catalyst comprises one or more of palladium(II)acetate, bis(triphenylphosphine) palladium(II)chloride, Tetrakis(triphynylphosphine)palladium(0), Tris(dibenzylideneacetone) dipalladium(0), Bis (dibenzylideneacetone) dipalladium(0), Palladium(II) chloride. In particular, the palladium(II)acetate may be used.

In general, the ligand comprises BINAP, Xantphos, triphenylphosphine, tributylphosphine and XPhos. In particular, BINAP may be used.

In general, the solvent comprises one or more of xylene, toluene, ethylbenzene, methylene dichloride, ethylene dichloride, chloroform, carbon tetrachloride, ethyl acetate, butyl acetate, and isopropyl acetate or mixtures thereof. In particular, the solvent toluene may be used.

In general, the compound 3a is reacted with diphenylmethanimine in the presence of an amine protecting reagent to obtain pure compound 2a. The presence of an amine protecting reagent resulted in the reduction of impurity formation. The amine protecting agent is selected from tert-butyl dicarbonate (BOC), fluorenylmethyloxycarbonyl chloride (Fmoc-Cl), 9-fluorenylmethylsuccinimidyl carbonate (Fmoc-OSu), benzyl chloroformate (Cbz-Cl), dibenzyl pyrocarbonate (Cbz anhydride), acetyl chloride, acetic anhydride, trifluoroacetic anhydride (TFAA), phthalic anhydride, benzyl chloride, triphenylmethyl chloride and tosyl chloride. In particular, tert-butyl dicarbonate may be used.

In general, the compound 2a is reacted with hydrochloric acid to obtain compound 5 in one or more solvents.

In general, the solvent comprises one or more of methanol, ethanol, isopropanol, butanol, acetone, methyl ethyl ketone, methyl isobutyl ketone, ethyl acetate, isopropyl acetate, butyl acetate, methylene dichloride, toluene, xylene, ethylbenzene, dimethylformamide, dimethylacetamide, dimethylsulfoxide, 1,4-dioxane, tetrahydrofuran, acetonitrile, water or mixtures thereof. In particular, the solvent is a mixture of water and toluene.

In general, the compound 5 may be extracted with one or more solvents. The compound 5 as monohydrate may be obtained by the removal of solvents after extraction and crystallizing the residue with one or more solvents.

The solvent for extraction is selected from methylene dichloride, toluene, ethyl acetate, methyl tert-butyl ether, 1,4-dioxane, cyclohexane, diethylether, tetrahydrofuran, or mixtures thereof. In particular, the reaction mixture is extracted with methylene dichloride.

In general, the compound 4a is reacted with cyclopropanecarboxylic acid in the presence of sulphuric acid and ammonium persulfate and silver nitrate in water to obtain compound 3a. The compound 3a is reacted with diphenylmethanimine in presence of BINAP, palladium acetate, STB in toluene which is further reacted with conc. HCl to obtain compound 5 and isolated as hydrate. In particular, as monohydrate.

In general, wherever not specified, the reaction may be performed in the presence of one or more solvents comprises of water, alcohols selected from methanol, ethanol, isopropanol, and n-butanol; esters selected from ethyl acetate, isopropyl acetate, t-butyl acetate, and isobutyl acetate; ketones selected from acetone, methyl ethyl ketone and methyl isobutyl ketone; hydrocarbons selected from toluene, xylene, ethyl benzene, heptane, hexane, and cyclohexane; halogenated hydrocarbons selected from methylene dichloride, ethylene dichloride, chlorobenzene, chloroform, and carbon tetrachloride; nitriles selected from acetonitrile and propanenitrile.

In another general aspect, there is provided a process for crystallizing the intermediate compounds of the present invention and avoid flash chromatography techniques reported in the prior art.

In another general aspect, there is provided a process for the preparation of compound 6,

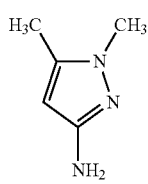
6 the process comprising:
(a) halogenating 2-butenenitrile to obtain compound 2,3-dihalobutanenitrile; and
(b) reacting the compound 2,3-dihalobutanenitrile with methyl hydrazine or salts thereof in the presence of a base to obtain compound 6.

In general, the compound 2-butenenitrile may be halogenated via halogenation comprises chlorination, bromination, fluorination, or iodination. In particular, the halogenation comprises bromination using a brominating agent selected from bromine, HBr-Acetic acid, 1,4-dibromo-dimethylhydantoin, N-bromosuccinimide. In particular, bromine may be used.

In general, the compound 2,3-dihalobutanenitrile obtained in step (a) is 2,3-dibromobutanenitrile.

In general, the compound 2,3-dibromobutanenitrile is further reacted with methyl hydrazine sulphate in the presence of a base to obtain a compound 6.

In general, the base comprises one or more of sodium hydroxide, potassium hydroxide, lithium hydroxide, barium hydroxide, sodium carbonate, potassium carbonate, barium carbonate, cesium carbonate, sodium bicarbonate, potassium bicarbonate, STB, PTB, pyridine, piperidine, morpholine, TEA, DIPEA, DBU, or DABCO. In particular, the sodium hydroxide may be used.

In general, wherever not specified, the reaction may be performed in the presence of one or more solvents comprises of water, alcohols selected from methanol, ethanol, isopropanol, and n-butanol; esters selected from ethyl acetate, isopropyl acetate, t-butyl acetate, and isobutyl acetate; ketones selected from acetone, methyl ethyl ketone and methyl isobutyl ketone; hydrocarbons selected from toluene, xylene, ethyl benzene, heptane, hexane, and cyclohexane; halogenated hydrocarbons selected from methylene dichloride, ethylene dichloride, chlorobenzene, chloroform, and carbon tetrachloride; nitriles selected from acetonitrile and propanenitrile.

In another general aspect, there is provided a triaminopyrimidine compound 1 having a purity of about 98% or more, of about 99% or more, of about 99.5% or more, of about 99.8% or more, by weight by area percentage by HPLC.

In another general aspect, there is provided a triaminopyrimidine compound 1 having a purity of about 99% or more and total impurities of about 1.0% or less, by area percentage of HPLC.

In another general aspect, there is provided a triaminopyrimidine compound 1 having a purity of about 99.6% or more, and total impurities of about 0.4% or less, by area percentage of HPLC.

In general, the triaminopyrimidine compound 1 is substantially free from one or more of compound 11, compound 12, compound 13, compound 14 and compound 15 as below:

Compound 11: (R)-N²,N⁴-bis(1,5-dimethyl-1H-pyrazol-3-yl)-5-(3,4-dimethyl-piperazin-1-yl)pyrimidine-2,4-diamine;

Compound 12: (R)-N²,N⁴-bis(4-cyclopropyl-5-fluoro-6-methylpyridin-2-yl)-5-(3,4-dimethylpiperazin-1-yl)pyrimidine-2,4-diamine;

Compound 13: (R)-4-cyclopropyl-6-((4-((1,5-dimethyl-1H-pyrazol-3-yl)amino)-5-(3,4-dimethylpiperazin-1-yl)pyrimidin-2-yl)amino)-3-fluoro-2-methylpyridine 1-oxide;

Compound 14: (R)-N⁴-(1,5-dimethyl-1H-pyrazol-3-yl)-5-(3,4-dimethylpiperazin-1-yl)-N²-(5-fluoro-6-methylpyridin-2-yl)pyrimidine-2,4-diamine;

Compound 15: (S)-N²-(4-cyclopropyl-5-fluoro-6-methylpyridin-2-yl)-N⁴-(1,5-dimethyl-1H-pyrazol-3-yl)-5-(3,4-dimethylpiperazin-1-yl)pyrimidine-2,4-diamine.

In another general aspect, there is provided substantially pure triaminopyrimidine compound 1 substantially free from one or more of the following compounds:

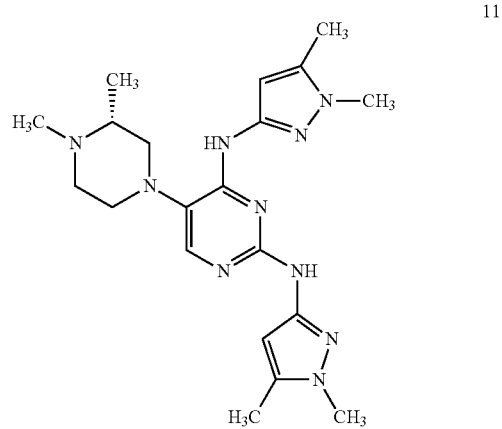
11

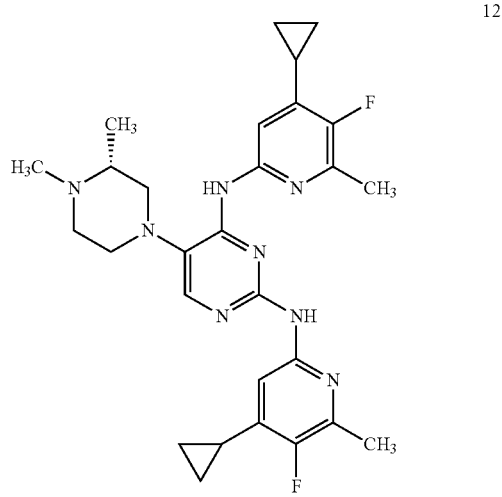
12

-continued

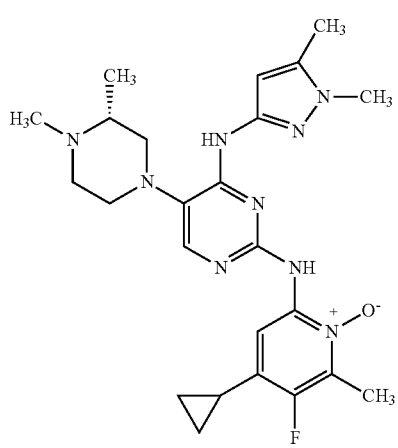

13

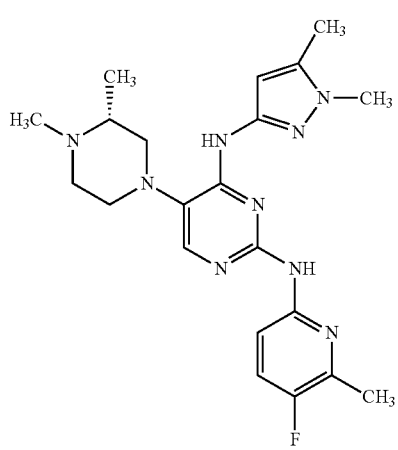

14

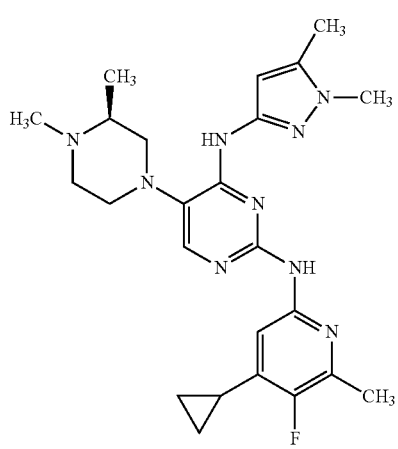

15

In general, the results of the analysis using HPLC of the compounds prepared by the process of the present invention has total impurities of about 1.0% or less, particularly of about 0.8% or less, more particularly, more particularly about 0.4% or less, still more particularly about 0.2% or less, by area percentage of HPLC and having a purity of about 99% or more, particularly of about 99.2% or more, more particularly of about 99.6% or more, still more particularly of about 99.8% or more, by weight by area percentage of HPLC.

In another general aspect, there is provided a composition comprising triaminopyrimidine compound 1 having a purity of about 99% or more by weight, and (S)-N²-(4-cyclopropyl-5-fluoro-6-methylpyridin-2-yl)-N⁴-(1,5-dimethyl-1H-pyrazol-3-yl)-5-(3,4-dimethylpiperazin-1-yl)pyrimidine-2,4-diamine (relative to triaminopyrimidine) in an amount of about 0.5% or less, by weight, by area percentage of HPLC.

In general, the composition comprises (S)-N²-(4-cyclopropyl-5-fluoro-6-methylpyridin-2-yl)-N⁴-(1,5-dimethyl-1H-pyrazol-3-yl)-5-(3,4-dimethyl piperazin-1-yl)pyrimidine-2,4-diamine relative to triaminopyrimidine compound 1 in an amount of about 0.25% or less, or of about 0.20% or less, or of about 0.15% or less, by weight by area percentage of HPLC.

In another general aspect, there is provided a composition comprising: triaminopyrimidine compound 1 having a purity of greater than or equal to 99% by weight, and (R)-4-cyclopropyl-6-((4-((1,5-dimethyl-1H-pyrazol-3-yl)amino)-5-(3,4-dimethylpiperazin-1-yl)pyrimidin-2-yl)amino)-3-fluoro-2-methylpyridine 1-oxide present (relative to triaminopyrimidine) in an amount of about 0.5% or less by weight, by area percentage of HPLC.

In general, the composition comprises (R)-4-cyclopropyl-6-((4-((1,5-dimethyl-1H-pyrazol-3-yl)amino)-5-(3,4-dimethylpiperazin-1-yl)pyrimidin-2-yl)amino)-3-fluoro-2-methylpyridine 1-oxide relative to triaminopyrimidine compound 1 in an amount of about 0.25% or less, or of about 0.20% or less, or of about 0.15% or less, by weight by area percentage of HPLC.

In general, the compositions as herein above comprising triaminopyrimidine compound 1 having a purity of about 98% or more, of about 99% or more, of about 99.5% or more, of about 99.8% of more, of about 99.9% or more, by weight by area percentage of HPLC.

In another general aspect, there is provided a process for the preparation of triaminopyrimidine compound 1, the process comprising:
(a) reacting compound 10 with compound 9 in one or more solvents to obtain a compound 8;

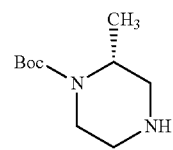

10

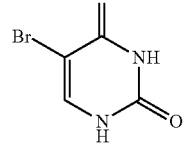

9

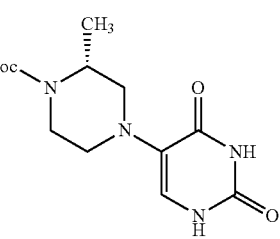

8

(b) reacting the compound 8 with a chlorinating agent in one or more solvents to obtain compound 7;

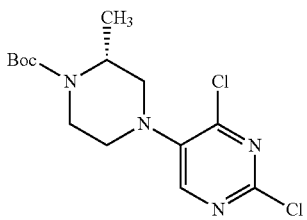
7

(c) reacting the compound 7 with compound 6 in one or more solvents in the presence of a base to obtain compound 4;

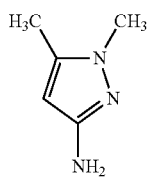
6

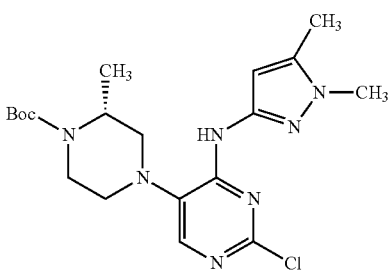
4

(d) reacting the compound 4 with compound 5 in one or more solvents in the presence of a base to obtain compound 3 or solution thereof;

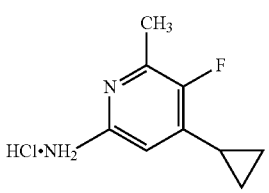
5

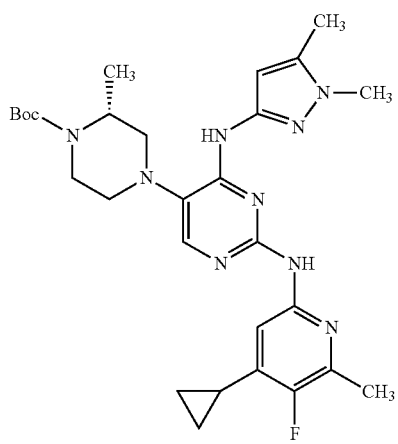
3

(e) reacting the compound 3 or solution thereof with an acid in one or more solvents to obtain compound 2 free base;

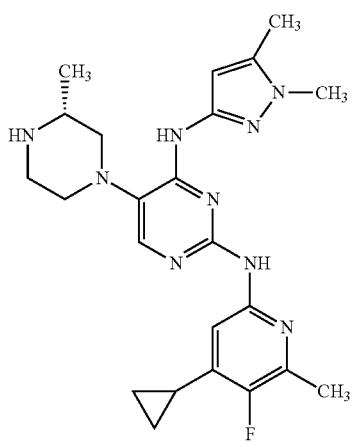
2

(f) reacting the compound 2 free base with a methylating agent in one or more solvents to obtain the compound 1; and (g) optionally crystallizing the compound in one or more solvents.

In general, the compound 10 and the compound 9 can be reacted in the presence of one or more solvents and a base.

Base comprises one or more of sodium hydroxide, potassium hydroxide, lithium hydroxide, barium hydroxide, sodium carbonate, potassium carbonate, barium carbonate, cesium carbonate, sodium bicarbonate, potassium bicarbonate, pyridine, piperidine, morpholine, TEA, DIPEA, DBU, STB, PTB, or DABCO. In particular, pyridine, TEA or DIPEA may be used.

Solvent comprises one or more of methanol, ethanol, isopropanol, butanol, acetone, methyl ethyl ketone, methyl isobutyl ketone, ethyl acetate, isopropyl acetate, butyl acetate, methylene dichloride, toluene, xylene, ethylbenzene, dimethylformamide, dimethylacetamide, dimethylsulfoxide, 1,4-dioxane, tetrahydrofuran, acetonitrile, pyridine, TEA, DIPEA and water, or mixtures thereof. In particular, pyridine is used.

Preferably, the reaction of the compound 10 and the compound 9 is carried out at about 40° C. to about reflux temperature of the solvent. In particular, the reaction may be carried out at 110 to 115° C. in pyridine for 5 to 15 hours to obtain compound 8.

In general, the compound 8 is reacted with a chlorinating reagent in the presence of a catalyst in one or more solvents. The chlorinating reagent is selected from phosphorus oxychloride, phosphorus pentachloride, phosphorus trichloride, and thionyl chloride. In particular, phosphorus oxychloride may be used.

In general, the catalyst is selected from the group consisting of pyridine, N,N-dimethyl aniline, N,N-diethyl aniline, and DIPEA. In particular, pyridine is used.

In general, the solvent comprises one or more of xylene, toluene, ethylbenzene, methylene dichloride, ethylene dichloride, chloroform, carbon tetrachloride, ethyl acetate, butyl acetate, isopropyl acetate, phosphorus oxychloride and thionyl chloride or mixtures thereof. In particular, the solvent is phosphorus oxychloride.

In general, the compound 8 is reacted with phosphorus oxychloride in the presence of catalytic amount of pyridine at 110 to 115° C. to obtain intermediate compound which is then reacted with one or more protecting agent selected from tert-butyl dicarbonate (BOC), fluorenylmethyloxycarbonyl chloride (Fmoc-Cl), 9-fluorenylmethylsuccinimidyl carbonate (Fmoc-OSu), benzyl chloroformate (Cbz-Cl), dibenzyl pyrocarbonate (Cbz anhydride), acetyl chloride, acetic anhydride, Trifluoroacetic anhydride (TFAA), phthalic anhydride, benzyl chloride, triphenylmethyl chloride, tosyl chloride, in one or more solvent to obtain compound 7. In particular, tert-butyl dicarbonate may be used.

In general, the solvent for the preparation of compound 7 comprises one or more of methanol, ethanol, isopropanol, butanol, acetone, methyl ethyl ketone, methyl isobutyl ketone, ethyl acetate, isopropyl acetate, butyl acetate, methylene dichloride, chloroform, toluene, water, or mixtures thereof. In particular, the mixture of ethyl acetate and water may be used.

The compound 7 may be isolated by removing ethyl acetate from the reaction mixture and treating with one or more alcohols selected from methanol, ethanol, isopropanol, butanol or water, or mixtures thereof.

The reaction of compound 7 with compound 6 is carried out in the presence of a base in one or more solvents.

In general, the base comprises one or more of sodium hydroxide, potassium hydroxide, lithium hydroxide, barium hydroxide, sodium carbonate, potassium carbonate, barium carbonate, cesium carbonate, sodium bicarbonate, potassium bicarbonate, pyridine, piperidine, morpholine, TEA, DIPEA, DBU, STB, PTB, or DABCO. In particular, the cesium carbonate may be used.

In general, the solvent comprises one or more of methanol, ethanol, isopropanol, butanol, acetone, methyl ethyl ketone, methyl isobutyl ketone, ethyl acetate, isopropyl acetate, butyl acetate, methylene dichloride, toluene, xylene, ethylbenzene, dimethylformamide, dimethylacetamide, dimethylsulfoxide, 1,4-dioxane, tetrahydrofuran, acetonitrile and water, or mixtures thereof. In particular, the solvent is toluene.

In general, the reaction of compound 7 with compound 6 may be performed in the presence of catalyst optionally in presence of a ligand. The catalyst comprises one or more of Palladium(II)acetate, bis(triphenylphosphine)palladium(II) chloride, Tetrakis(triphenylphosphine)palladium(0), tris(dibenzylideneacetone) dipalladium(0), bis(dibenzylideneacetone)dipalladium(0), Palladium(II)chloride. The ligand comprises BINAP, Xantphos, triphenylphosphine, tributylphosphine and Xphos.

In general, the compound 7 is reacted with compound 6 in toluene and in the presence of cesium carbonate, palladium(II)acetate and BINAP at 110 to 115° C. for 5 to 20 hours, in particular for 16 hours to obtain the compound 4.

In general, the pure compound 4 can be isolated from the reaction mixture by adsorbing the crude solution on silica gel followed by removal of solvent and extraction with ethyl acetate, hexane, or mixtures thereof.

In general, the compound 4 is reacted with compound 5 as monohydrate in one or more solvents in the presence of a base to obtain compound 3.

In general, the base comprises one or more of sodium hydroxide, potassium hydroxide, lithium hydroxide, barium hydroxide, sodium carbonate, potassium carbonate, barium carbonate, cesium carbonate, sodium bicarbonate, potassium bicarbonate, STB, PTB, pyridine, piperidine, morpholine, TEA, DIPEA, DBU, or DABCO. In particular, the cesium carbonate may be used.

In general, the solvent comprises one or more of methanol, ethanol, isopropanol, butanol, acetone, methyl ethyl ketone, methyl isobutyl ketone, ethyl acetate, isopropyl acetate, butyl acetate, methylene dichloride, toluene, xylene, ethylbenzene, dimethylformamide, dimethylacetamide, dimethylsulfoxide, 1,4-dioxane, tetrahydrofuran, acetonitrile and water, or mixtures thereof. In particular, the solvent is toluene.

In general, the reaction of the compound 4 with the compound 5 or a hydrate thereof may be performed in the presence of catalyst optionally in presence of ligand. The catalyst comprises one or more of palladium(II)acetate, bis(triphenyl-phosphine) palladium(II)chloride, tetrakis(triphenylphosphine)palladium(0), tris(dibenzyli-deneacetone) dipalladium(0), bis(dibenzylideneacetone)dipalladium(0), Palladium(II)acetate. The ligand comprises BINAP, Xantphos, triphenyl-phosphine, tributylphosphine and Xphos.

In general, the compound 4 is reacted with the compound 5 monohydrate in the presence of cesium carbonate in the presence of palladium acetate and BINAP in toluene at 110 to 115° C. for 7 to 15 H to obtain the compound 3.

In general, the pure compound 3 is isolated from reaction mixture by adsorbing compound 3 on silica gel followed by removal of solvent and extraction with ethyl acetate.

In general, the solution containing compound 3 obtained in step (d) can be used in step (R) without further purification or treatment or isolation.

In general, the compound 3 or solution thereof is further reacted with an acid to obtain free base compound 2. The reaction may be performed in the presence of one or more solvents.

In general, the acid comprises one or more of hydrochloric acid, hydrobromic acid, acetic acid, phosphoric acid, and trifluoroacetic acid. In particular, hydrochloric acid may be used.

In general, the solvent comprises one or more of methanol, ethanol, isopropanol, butanol, acetone, methyl ethyl ketone, methyl isobutyl ketone, ethyl acetate, isopropyl acetate, butyl acetate, methylene dichloride, toluene, xylene, ethylbenzene, dimethylformamide, dimethylacetamide, dimethylsulfoxide, 1,4-dioxane, tetrahydrofuran, acetonitrile and water or mixtures thereof. In particular, the solvent is mixture containing toluene and water.

In general, the compound 3 is reacted with conc. hydrochloric acid in water at room temperature to about reflux temperature of solvent for sufficient time. The reaction mixture may be basified and extracted with one or more solvents to obtain compound 2. The compound 2 as free base may be obtained by removal of solvent after extraction and crystallizing the residue with one or more solvents.

In general, the reaction of compound 3 with conc. hydrochloric acid may be done at 25° C. to about 120° C. In particular, at about 50° C. to about 55° C.

The reaction mixture may be basified using one or more base selected from sodium hydroxide, potassium hydroxide, lithium hydroxide, barium hydroxide, sodium carbonate, potassium carbonate, barium carbonate, cesium carbonate, sodium bicarbonate, potassium bicarbonate. In particular, sodium carbonate may be used.

The solvent for extraction is selected from methylene dichloride, toluene, ethyl acetate, methyl tert-butyl ether, 1,4-dioxane, and tetrahydrofuran or mixtures thereof. In particular, the reaction mixture is extracted with methylene dichloride.

In general, there is provided a process for crystallizing free compound 2 comprising crystallizing from one or more solvents.

In general, the solvent for crystallization of compound 2 free base comprises one or more of methanol, ethanol, isopropanol, butanol, acetone, methyl ethyl ketone, methyl isobutyl ketone, isopropyl acetate, butyl acetate, dimethylformamide, dimethylacetamide, dimethylsulfoxide, acetonitrile, water, or mixtures thereof. In particular, the solvent is acetonitrile.

In another general aspect, there is provided a process for preparation of triaminopyrimidine compound 1 comprising methylating free base compound 2 with a methylating agent, optionally in the presence of a reducing agent, in one or more solvents.

In general, the compound 2 free base is reacted with methylating agent, optionally in the presence of a reducing agent, in one or more solvents to obtain the compound 1.

In general, the methylating agent comprises one or more of diazomethane, 2,2-dimethoxypropane, dimethyl carbonate, dimethyl sulfide, dimethyl zinc, methyl flouro sulfonate, methyl iodide, methyl bromide, methyltrifluoro methane sulfonate, trimethoxonium tetraflouroborate, formaldehyde, and mixture of formic acid and formaldehyde. In particular, the methylating agent is formaldehyde.

In general, the reducing agent comprises one or more of sodium cyanoborohydride, sodium triacetoxyborohydride, lithium aluminium hydride, and sodium borohydride.

In general, the compound 2 free base is reacted with formaldehyde in the presence of sodium triacetoxyborohydride to obtain the compound 1.

In general, the compound 2 free base is reacted with formaldehyde in the presence sodium triacetoxyborohydride to obtain compound 1. The reaction mixture may be basified and extracted with one or more solvents to obtain compound 1. The compound 1 may be obtained by removal of solvent after extraction and crystallizing the residue with one or more solvents.

In general, the reaction of compound 2 free base with formaldehyde may be done at 25° C. to about 120° C. In particular, at about 25° C. to about 35° C.

The reaction mixture may be basified using one or more base selected from sodium hydroxide, potassium hydroxide, lithium hydroxide, barium hydroxide, sodium carbonate, potassium carbonate, barium carbonate, cesium carbonate, sodium bicarbonate, and potassium bicarbonate. In particular, sodium carbonate may be used.

The solvent for extraction is selected from methylene dichloride, toluene, ethyl acetate, methyl tert-butyl ether, 1,4-dioxane, and tetrahydrofuran or mixtures thereof. In particular, the reaction mixture is extracted with methylene dichloride.

In general, the solvent for crystallization of compound 1 comprises one or more of methanol, ethanol, isopropanol, butanol, acetone, methyl ethyl ketone, methyl isobutyl ketone, isopropyl acetate, butyl acetate, dimethylformamide, dimethylacetamide, dimethylsulfoxide, acetonitrile, water or mixtures thereof. In particular, the solvent is acetonitrile.

In another general aspect, there in provided a process for the preparation of crystalline form of triaminopyrimidine compound 1, the process comprises crystallizing the triaminopyrimidine compound 1 in one or more solvents.

In general, the triaminopyrimidine compound 1 prepared during the reaction may be crystallized in-situ by solvent exchange or addition and removal of solvents or in the presence of another solvent, or triaminopyrimidine compound 1 may be isolated as solid compound and further crystallized in one or more solvents to obtain their solid state forms.

In general, the crystalline Form I of triaminopyrimidine compound 1 may be obtained by crystallization in one or more of methanol, ethanol, isopropanol, butanol, acetone, methyl ethyl ketone, methyl isobutyl ketone, isopropyl acetate, butyl acetate, dimethylformamide, dimethylacetamide, dimethylsulfoxide, acetonitrile, water or mixtures thereof. In particular, acetonitrile may be used.

In general, the crystalline Form II of triaminopyrimidine compound 1 may be obtained by crystallization in one or more methanol, ethanol, isopropanol, butanol, acetone, methyl ethyl ketone, methyl isobutyl ketone, isopropyl acetate, butyl acetate, dimethylformamide, dimethylacetamide, dimethylsulfoxide, acetonitrile, water or mixtures thereof. In particular, mixture of acetonitrile and water.

In general, the solvent for crystallization of compound 2 free base comprises one or more of methanol, ethanol, isopropanol, butanol, acetone, methyl ethyl ketone, methyl isobutyl ketone, isopropyl acetate, butyl acetate, dimethylformamide, dimethylacetamide, dimethylsulfoxide, acetonitrile, water or mixtures thereof. In particular, the solvent is acetonitrile.

In general, wherever not specified, the reaction may be performed in presence of one or more solvents comprises of water, alcohol selected from methanol, ethanol, isopropanol, and n-butanol; ester selected from ethyl acetate, isopropyl acetate, t-butyl acetate, and isobutyl acetate; ketone selected from acetone, methyl ethyl ketone and methyl isobutyl ketone; hydrocarbon selected from toluene, xylene, ethyl benzene, heptane, hexane, and cyclohexane; halogenated hydrocarbon selected from methylene dichloride, ethylene dichloride, chlorobenzene, chloroform, and carbon tetrachloride; nitriles selected from acetonitrile and propanenitrile.

In another general aspect, there is provided a process for crystallizing the intermediate compounds of the present invention and avoid flash chromatography techniques reported in the prior art.

In further general aspect, there is provided a process for the preparation of triaminopyrimidine compound 1 of the present invention in crystalline form thereby avoiding microwave irradiation conditions as reported in the prior art.

In another general aspect, there is provided a pharmaceutical composition comprising crystalline triaminopyrimidine compound 1 and pharmaceutically acceptable carrier, diluents and excipients.

In another general aspect, there is provided a pharmaceutical composition comprising substantially pure triaminopyrimidine compound 1 and one or more of pharmaceutically acceptable carrier, diluents and excipients.

In general, the pharmaceutical composition of the present invention may be in the form of a solid or liquid dosage forms for oral, parenteral or topical use and may have immediate or sustained release characteristics. The dosage forms possible include powders, granules, creams, tablets, capsules, injectable, solutions, elixirs or suspensions.

Powder X-ray diffraction of triaminopyrimidine compound 1 and compound 5 can be obtained under following conditions.

The powder x-ray diffraction pattern can be measured using PANalytical ExpertPro x-ray diffractometer, or Bruker, or Philips, or any other equivalent make, and having CuKα source.

Differential Scanning calorimetry of triaminopyrimidine compound 1 and compound 5 can be obtained under following conditions.

Differential scanning calorimetric analysis can be performed using a Perkin Elmer DSC control unit and a DSC 300° C. differential scanning calorimeter. 2-5 mg samples were placed in crimped aluminum pans and heated from 50° C. to 300° C. in a liquid nitrogen atmosphere at a heating rate of 10° C./minute. Zinc-Indium or any other suitable reference may be as the standard substance.

The examples are set forth to aid in understanding the invention but are not intended to, and should not be construed to limit its scope in any way. The examples do not include detailed descriptions of conventional methods. Such methods are well known to those of ordinary skill in the art and are described in numerous publications.

EXAMPLES: PREPARATION OF INTERMEDIATES

Example-1: Preparation of 6-chloro-4-cyclopropyl-3-fluoro-2-methylpyridine

In a 250 mL 4N round bottom flask, process water (30 ml) and cyclopropanecarboxylic acid (14.19 g, 164.88 mmol) were added at 25 to 35° C. and started stirring. Sulphuric acid (4.4 ml, 82.44 mmol) was charged to the reaction mixture. Silver nitrate (4.18 g, 24.73 mmol), 6-Chloro-3-fluoro-2-methylpyridine (6 g, 41.22 mmol) were charged to the reaction mixture. Aqueous solution of ammonium persulphate (65.85 g, 288.54 mmol in 90 mL water) was added to the reaction mixture in 30 to 60 min at temperature NMT 60° C. After the completion of the reaction as monitored by HPLC, toluene (30 ml) was added to the reaction mixture and stirred for 15 min. The reaction mixture filtered, separated layers from filtrate and extracted aqueous layer using toluene (30 mL). The organic layer was washed with aqueous sodium carbonate solution (30 mL) and water. The organic layer was distilled completely under vacuum at 60° C. to obtain 3.37 g syrupy mass as titled compound.

Example-2: Preparation of 6-chloro-4-cyclopropyl-3-fluoro-2-methylpyridine

In a suitable glass assembly, process water (7.5 L) and cyclopropanecarboxylic acid (3.55 Kg, 41.24 mol) were added at 25 to 35° C. and stirred. Sulphuric acid (2.02 Kg, 20.59 mol), silver nitrate (1.05 Kg, 6.21 mol), 6-chloro-3-fluoro-2-methylpyridine (1.5 Kg, 10.3 mol) were added to the reaction mixture. Aqueous solution of ammonium persulphate (16.46 g, 72.13 mmol in 22.5 L water) was added to the reaction mixture at 55 to 60° C. and maintained. After the completion of the reaction as monitored by HPLC, toluene (7.5 L) was added to the reaction mixture and stirred for 15 min. The reaction mixture was filtered, organic layer was separated and aqueous layer was extracted using toluene (6 L), filtered the reaction mixture and washed the solid with toluene (1.5 L). The combined organic layer was washed with 20% sodium carbonate solution (9 L) and water. The organic layer was concentrated completely under vacuum at 60° C. to obtain 880 g (86.50%) syrupy mass of titled compound.

Example-3: Preparation of N-(4-cyclopropyl-5-fluoro-6-methylpyridin-2-yl)-1,1-diphenyl-methanimine In a 100 mL 3N round bottom flask, 6-chloro-4-cyclopropyl-3-fluoro-2-methylpyridine (2.69 g, 14.48 mmol) and toluene (30 mL) were added at 25 to 35° C. Diphenylmethanimine (3.15 g, 17.38 mmol) was charged to the reaction mixture and stirred for 5-10 min under nitrogen purging. Racemic BINAP (270 mg, 0.43 mmol) and palladium acetate (98 mg, 0.43 mmol) were added to the reaction mixture. Sodium-tert-butoxide (2.78 g, 28.96 mmol) was added to the reaction mixture and heated to 100 to 110° C. under nitrogen. After the completion of the reaction as monitored by HPLC, the reaction mixture was cooled to 25 to 35° C. and filtered over hyflo bed and washed with toluene. The filtrate containing titled compound was preserved for next stage of reaction.

Example-4: Preparation of N-(4-cyclopropyl-5-fluoro-6-methylpyridin-2-yl)-1,1-diphenyl-methanimine In a suitable assembly, 6-chloro-4-cyclopropyl-3-fluoro-2-methylpyridine (880) and toluene (7.5 L) were added at 25 to 35° C. Diphenylmethanimine (787 g, 4.34 mmol) and BOC anhydride (237 g, 1.086 mol) was added to the reaction mixture and stirred for 5-10 min under nitrogen purging. Racemic BINAP (67.6 g, 0.108 mmol) and palladium acetate (24.4 g, 0.108 mol) were added to the reaction mixture. Sodium-tert-butoxide (870 g, 9.05 mol) was added to the reaction mixture and heated to 100 to 110° C. under nitrogen. After the completion of the reaction as monitored by HPLC, the reaction mixture was cooled to 25 to 35° C., water (6 L) was added. The reaction mixture was filtered over hyflo bed and washed with toluene. The filtrate containing titled compound was preserved for next stage of reaction.

Example-5: Preparation of 4-cyclopropyl-5-fluoro-6-methylpyridin-2-amine hydrochloride monohydrate In a 100 mL 3N round bottom flask, N-(4-cyclopropyl-5-fluoro-6-methylpyridin-2-yl)-1,1-diphenylmethanimine in toluene as obtained in example-3 was added water (25 mL) at 25 to 35° C. The conc. HCl (3 mL) was charged to the reaction mixture and heated to 40 to 50° C. After the completion of the reaction as monitored by HPLC, the reaction mixture was cooled to 25 to 35° C. Layers were separated. The aqueous layer was treated with methylene dichloride and pH was adjusted to 7.5 to 8.5 using sodium carbonate solution, stirred for 15 min and layers were separated. Aqueous layer was extracted with methylene dichloride, charcoaled and acidified to pH 3 to 4 with aqueous HCl. The solvent was distilled completely and acetonitrile (9 mL) and ethyl acetate (9 mL) was added. The reaction mixture was stirred for 1 hour at 25 to 35° C. The product was filtered and washed with ethyl acetate. The product was dried at 50° C. for 4 hours under vacuum to obtain 1.62 g title compound as monohydrate yellow crystalline solid having 99.51% HPLC purity.

Example-6: Preparation of 4-cyclopropyl-5-fluoro-6-methylpyridin-2-amine hydrochloride monohydrate In a suitable glass assembly, N-(4-cyclopropyl-5-fluoro-6-methylpyridin-2-yl)-1,1-diphenylmethanimine in toluene as obtained in example-4 was added water (6 L) at 25 to 35° C. The conc. HCl (750 mL) was charged to the reaction mixture and heated to 40 to 50° C. After the completion of the reaction as monitored by HPLC, the reaction mixture was cooled to 25 to 35° C. Layers were separated. The aqueous layer was treated with methylene dichloride (3 L) and pH was adjusted to 7.5 to 8.5 using sodium carbonate solution, stirred for 15 min and layers were separated. Aqueous layer was extracted with methylene dichloride (3 L), charcoaled and acidified to pH 3 to 4 with aqueous HCl. The solvent was distilled completely and acetonitrile (1.5 L) and ethyl acetate (1.5 L) were added. The reaction mixture was stirred for 1 hour at 25 to 35° C. The product was filtered and washed with ethyl acetate. The product was dried at 50° C. for 4 hours under vacuum to obtain 489 g (96.80%) title compound as monohydrate yellow crystalline solid having 99.51% HPLC purity. The crystalline compound is characterized by Powder x-ray diffraction pattern (FIG. 5), Differential scanning calorimetry (FIG. 6) and Thermogravimetric analysis (FIG. 7).

Example 7: Preparation of 2,3-dibromobutanenitrile

In a 2 L round bottom flask, dichloromethane (550 mL) and 2-butenenitrile 110 g (1.64 mol) were cooled to 20 to 25° C. A solution of bromine 275 g (1.72 mol) in dichloromethane (220 mL) was dropwise added at 20 to 25° C. Hydrobromic acid 1.43 ml (0.0082 mol) in acetic acid (33%) solution was added into the reaction mixture and stirred for 4 hours. After the completion of reaction, $Na_2S_2O_3$ (550 mL) 4% aqueous solution was added and the reaction mixture was stirred for 15 min. The separated organic layer was distilled under vacuum completely to obtain 364.2 g (97.9%) of title compound as an oil.

Example 8: Preparation of 1,5-dimethyl-1H-pyrazol-3-amine

In a 5 L round bottom flask, water (1.36 L), sodium hydroxide 340 g (8.99 mol) were added and the reaction mixture was cooled to 0 to 5° C. A solution of methyl hydrazine sulphate 237.8 g (1.65 mol) in 680 mL water was added dropwise to the reaction mixture and stirred below 10° C. 2,3-dibromobutanenitrile 340 g (1.5 mol) prepared in example-7 was added and the reaction mixture was stirred below 10° C. for 2 hours. After the completion of reaction, toluene (630 mL) was added and the reaction mixture was stirred for 15 min. The aqueous layer was separated and the organic layer was removed. The aqueous layer was extracted with dichloromethane (5.1 L). The combined organic layer was distilled completely under vacuum to obtain residue. Diisopropyl ether (680 mL) was added and the reaction mixture was stirred at 0 to 5° C. for 1 hour. The reaction mixture was filtered, washed with diisopropyl ether and dried to obtained 121.5 g (72.93%) of title compound having 95.63% purity.

Examples: Preparation of Triaminopyrimidine Compounds

Example-9: Preparation of tert-butyl (R)-4-(2,4-dioxo-1,2,3,4-tetrahydro-pyrimidin-5-yl)-2-methylpiperazine-1-carboxylate In 2 L four neck round bottom flask, 1.25 Kg (6.545 mol) 5-bromouracil, 1.87 Kg (9.360 mol) tert-butyl (R)-2-methylpiperazine-1-carboxylate and 5 L pyridine were added at 25 to 35° C. The reaction mass was stirred for 15 hours at 115 to 120° C. After completion, the reaction mass was cooled to 25 to 35° C. 12.5 L water was added and stirred for 1 hour. The reaction mass was filtered, washed with 2.5 L water and dried to obtain 1.37 Kg (67.4%) of title compound.

Example-10: Preparation of tert-butyl (R)-4-(2,4-dichloropyrimidin-5-yl)-2-methylpiperazine-1-carboxylate In 20 L four neck round bottom flask, 1.36 Kg (4.382 mmol) tert-butyl (R)-4-(2,4-dioxo-1,2,3,4-tetrahydropyrimidin-5-yl)-2-methylpiperazine-1-carboxylate and 6.8 L phosphorus oxychloride were added at 25 to 35° C. 26.5 mL pyridine (0.329 mol) was added and the reaction mass was heated to 105 to 110° C. and stirred for 4 hours. After the completion of the reaction, phosphorus oxychloride was distilled completely at atmospheric pressure. 2.72 L acetone was added and the reaction mixture was quenched into 4.08 L water. Acetone was removed by distillation under vacuum. 20% sodium carbonate solution was added to adjust pH 7.5-8.5 of the reaction mixture. 1.14 Kg (5.258 mol) di-tert-butyl dicarbonate and 9.52 L ethyl acetate were added and stirred for 2 hours at 25 to 35° C. After the completion of the reaction, the organic layer was separated and aqueous layer was extracted with 6.8 L ethyl acetate. The combined ethyl layers were distilled to remove ethyl acetate completely under vacuum to obtain residue. 1.36 L isopropyl alcohol was added to the residue and isopropyl alcohol was removed completely. 4.08 L isopropyl alcohol and 6.8 L water were added to the residue and stirred for 1 hour. The reaction mass was filtered, washed with water and dried to obtain 1.25 Kg of title compound.

Example-11: Preparation of tert-butyl (R)-4-(2-chloro-4-[(1,5-dimethyl-1H-pyrazol-3-yl)amino)pyrimidin-5-yl]-2-methylpiperazine-1-carboxylate In 20 L round bottom flask, 640 g (1.843 mol) tert-butyl (R)-4-(2,4-dichloropyrimidin-5-yl)-2-methylpiperazine-1-carboxylate, 225.3 g (2.027 g) 1,5-dimethyl-1H-pyrazol-3-amine and 9.6 L toluene were added at 25 to 35° C. 1.2 Kg (3.686 mol) cesium carbonate was added. The reaction mixture was purged for 15 min under nitrogen. 12.41 g (0.0553 mol) palladium acetate and 34.43 g (0.0553 mol) racemic 2,2'-bis(diphenylphosphino)-1,1'-binaphthyl were added and the reaction mass was maintained for 16 hours at 110 to 115° C. under nitrogen. After the completion of the reaction, the reaction mixture was filtered through a celite bed and washed the bed with 1.28 L toluene. Toluene was distilled completely and 2.56 L dichlromethane was added. The compound was adsorbed by 1.92 Kg silica gel (60-120 mesh). The dichloromethane was distilled completely under vacuum and 12.8 L mixture of ethyl acetate and hexane was added to the residue and stirred for 2 hours. The silica gel was filtered and the filtrate was distilled completely under vacuum to obtain 595 g title compound.

Example-12: Preparation of tert-butyl (R)-4-(2-((4-cyclopropyl-5-fluoro-6-methylpyridin-2-yl)amino)-4-((1,5-dimethyl-1H-pyrazol-3-yl)amino) pyrimidin-5-yl)-2-methylpiperazine-1-carboxylate In 20 L round bottom flask, 595 g (1.40 mol) tert-butyl (R)-4-(2-chloro-4-[(1,5-dimethyl-1H-pyrazol-3-yl)amino) pyrimidin-5-yl]-2-methylpiperazine-1-carboxylate, 305 g (1.38 mol) 4-cyclopropyl-5-fluoro-6-methylpyridin-2-amine hydrochloride and 11.5 L toluene were added at 25 to 35° C. 1.08 Kg (3.32 mol) cesium carbonate was added. The reaction mixture was purged for 15 min under nitrogen. 17.21 g (27.6 mmol) palladium acetate and 6.21 g (27.6 mmol) racemic 2,2'-bis(diphenylphosphino)-1,1'-binaphthyl were added. The reaction mass was stirred for 6 hours at 110 to115° C. under nitrogen. After the completion of the reaction, the reaction mixture was filtered through a celite bed and washed with toluene. The filtrate was used as such in the next step without further treatment.

Example-13: Preparation of tert-butyl (R)-4-(2-((4-cyclopropyl-5-fluoro-6-methylpyridin-2-yl)amino)-4-((1,5-dimethyl-1H-pyrazol-3-yl)amino) pyrimidin-5-yl)-2-methylpiperazine-1-carboxylate In 500 mL four neck round bottom flask, 7.5 g (17.77 mmol) (R)-tert-butyl 4-(2-chloro-4-[(1,5-dimethyl-1H-pyrazol-3-yl)amino)pyrimidin-5-yl]-2-methylpiperazine-1-carboxylate, 3.92 g (17.77 mmol) 4-cyclopropyl-5-fluoro-6-methylpyridin-2-amine hydrochloride compound and 150 mL toluene were added at 25 to 35° C. 20 g (61.3 mmol) cesium carbonate was added. The reaction mixture was purged for 15 min under nitrogen. Then, 130 mg (0.58 mmol) palladium acetate and 360 mg (0.58 mmol) racemic 2,2'-bis(diphenylphosphino)-1,1'-binaphthyl were added. The reaction mass was stirred for 18 hours at 110 to 115° C. under nitrogen. After completion, the reaction mixture was filtered through a celite bed and washed with toluene. The filtrate was used as such in the next step without further treatment.

Example-14: (R)-$N^2$-(4-cyclopropyl-5-fluoro-6-methylpyridin-2-yl)-$N^4$-(1,5-dimethyl-1H-pyrazol-3-yl)-5-(3-methylpiperazin-1-yl)pyrimidine-2,4-diamine In 50 L glass assembly, the filtrate containing tert-butyl (R)-4-(2-((4-cyclopropyl-5-fluoro-6-methylpyridin-2-yl)amino)-4-((1,5-dimethyl-1H-pyrazol-3-yl)amino) pyrimidin-5-yl)-2-methylpiperazine-1-carboxylate from example 13 was taken. 11.5 L water and 1.28 L Conc. HCl were added at 25 to 35° C. The reaction mass was stirred for 2 hours at 50 to 55° C. After the completion of the reaction, reaction mixture was cooled to room temperature and filtered over celite bed and washed with water. The separated the aqueous layer from filtrate was basified by using 20% sodium carbonate solution and extracted with 12.8 L methylene dichloride. The organic layer was distilled completely under vacuum to obtain residue. 9.6 L acetonitrile was added to the residue and heated to reflux for 30 min. The reaction mixture was cooled and stirred at 25 to 35° C. for 1 hour. The reaction mixture was filtered, washed with 640 mL acetonitrile and dried to obtain 360 g titled compound.

Example-15: (R)-$N^2$-(4-cyclopropyl-5-fluoro-6-methylpyridin-2-yl)-$N^4$-(1,5-dimethyl-1H-pyrazol-3-yl)-5-(3,4-dimethylpiperazin-1-yl)pyrimidine-2,4-diamine In 250 mL four neck round bottom flask, 4.7 g (10.4 mmol) (R)-$N^2$-(4-cyclopropyl-5-fluoro-6-methylpyridin-2-yl)-$N^4$-(1,5-dimethyl-1H-pyrazol-3-yl)-5-(3,4-dimethylpiperazin-1-yl)pyrimidine-2,4-diamine was dissolved in 56 mL ethanol. 1.89 g (23.32 mmol) formaldehyde and 1.44 g (22.90 mmol) sodium cyanoborohydride were added. Adjusted pH 5-6 using acetic acid and stirred the reaction mass at 25 to 35° C. for 2 hours. After completion, ethanol was distilled completely under vacuum. 47 mL water was added to the residue. The reaction mass was basified by 20% sodium carbonate solution and extracted with methylene dichloride. Both the organic layers were combined and distilled completely under vacuum. 94 mL acetonitrile was added to the residue and heated to reflux for 15 min. The reaction mass was cooled to 25 to 35° C. and stirred for 1 hour. The reaction mass was filtered, washed with 5 mL acetonitrile and dried to obtain 3.7 g title compound as crystalline solid, having HPLC purity of about 99.61%.

Example-16: (R)-$N^2$-(4-cyclopropyl-5-fluoro-6-methylpyridin-2-yl)-$N^4$-(1,5-dimethyl-1H-pyrazol-3-yl)-5-(3,4-dimethylpiperazin-1-yl)pyrimidine-2,4-diamine In 20 L round bottom flask, 725 g (1.60 mol) (R)-$N^2$-(4-cyclopropyl-5-fluoro-6-methylpyridin-2-yl)-$N^4$-(1,5-dimethyl-1H-pyrazol-3-yl)-5-(3,4-dimethylpiperazine-1-yl)pyrimidine-2,4-diamine was dissolved in 6.52 L dichloromethane. 261.5 g (3.2 mol) formaldehyde and 510.4 g (2.4 mol) sodium triacetoxyborohydride were added and stirred the reaction mixture at 25 to 35° C. for 2 hours. After the completion of the reaction, 3.63 L water was added into the reaction mixture. The reaction mixture was basified by 20% sodium carbonate solution and the organic layer was separated. The aqueous layer was extracted with 1.45 L methylene dichloride. The combined organic layers were distilled completely under vacuum. 14.5 L acetonitrile was added to the residue and heated to reflux for 15 min. The reaction mixture was cooled to 25 to 35° C. and stirred for 1 hour. The reaction mass was filtered, washed with 1.45 L acetonitrile and dried to obtain 632 g of title compound as crystalline solid having 99.01% HPLC purity. The crystalline compound is characterized by Powder x-ray diffraction pattern (FIG. 1) and Differential Scanning calorimetry (FIG. 2).

Example-17: Preparation of (R)-$N^2$-(4-cyclopropyl-5-fluoro-6-methylpyridin-2-yl)-$N^4$-(1,5-dimethyl-1H-pyrazol-3-yl)-5-(3,4-dimethylpiperazin-1-yl)pyrimidine-2,4-diamine In a 10 mL round bottom flask, 300 mg (0.644 mmol) (R)-$N^2$-(4-cyclopropyl-5-fluoro-6-methylpyridin-2-yl)-$N^4$-(1,5-dimethyl-1H-pyrazol-3-yl)-5-(3,4-dimethylpiperazin-1-yl)pyrimidine-2,4-diamine, 2.7 mL acetonitrile and 0.3 mL water were added and the reaction mixture was heated to reflux for 15 min. The reaction mixture was cooled to 25 to 35° C. and stirred for 1 hour. The reaction mass was filtered, washed with acetonitrile and dried to obtain 201 mg (67%) title compound as crystalline solid. The crystalline compound is characterized by Powder x-ray diffraction pattern (FIG. 3) and Differential Scanning calorimetry (FIG. 4).

While the present invention has been described in terms of its specific embodiments, certain modifications and equivalents will be apparent to those skilled in the art and are intended to be included within the scope of the present invention.

We claim:
1. A crystalline triaminopyrimidine compound of formula 1,

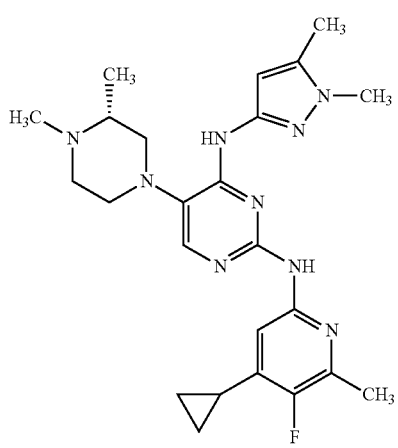

which is in crystalline Form I or Form II, wherein the crystalline Form I is characterized by a powder x-ray diffraction pattern having peaks expressed in degrees at 6.3°, 7.8°, 9.8°, 15.4°, and 20.0°±0.2° 2θ, when measured using CuKα source, and the crystalline Form II is characterized by a powder x-ray diffraction pattern having peaks expressed in degrees at 8.3°, 12.1°, 13.8°, 21.9°, and 23.7°±0.2° 2θ, when measured using CuKα source.

2. The crystalline triaminopyrimidine compound according to claim 1, which is in the crystalline Form I, wherein the crystalline Form I is further characterized by a differential scanning calorimetry analysis having onset at about 179° C.±5° C. and endothermic peak at about 181° C.±5° C., when the differential scanning calorimetry analysis is performed at a heating rate of 10° C./minute.

3. The crystalline triaminopyrimidine compound according to claim 1, which is in the crystalline Form II, wherein the crystalline Form II is further characterized by one or more of:
    (a) a differential scanning calorimetry analysis having at least one onset at about 161° C.±5° C. and endothermic peak at about 163° C.±5° C.;
    (b) a differential scanning calorimetry having one onset at about 161° C.±5° C. and second onset at about 179° C.±5° C.; and
    (c) a differential scanning calorimetry having one endothermic peak at about 163° C.±5° C. and second endothermic peak at about 181° C.±5° C.;
wherein the differential scanning calorimetry analysis in (a), (b), or (c) is performed at a heating rate of 10° C./minute.

4. A compound of formula 5,

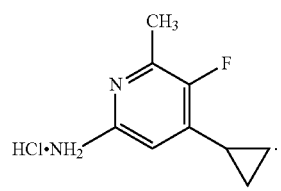

as crystalline monohydrate, characterized by a powder x-ray diffraction pattern having peaks expressed in degrees at 10.5°, 12.7°, 25.1°, and 25.7°±0.2° 2θ, wherein the powder x-ray diffraction pattern is obtained using CuKα source.

5. The compound according to claim 4 that is substantially pure having a purity of about 98% or more, by weight as measured by area percentage by HPLC.

6. The compound according to claim 4, wherein the compound is substantially free from one or more of compounds of formula 4b or formula 4c,

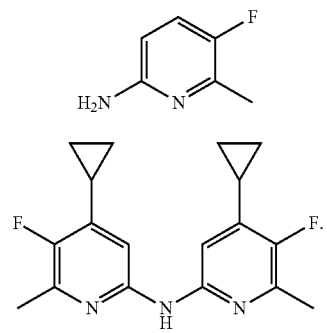

7. A process for the preparation of the compound of formula 5 according to claim 4,

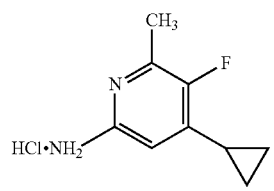

the process comprising:
(a) reacting compound of formula 4a with cyclopropane carboxylic acid in one or more solvents to obtain compound of formula 3a;

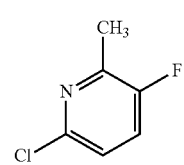

3a

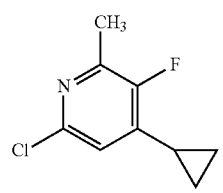

(b) reacting the compound of formula 3a with diphenyl-methanimine in one or more solvents to obtain compound of formula 2a;

2a

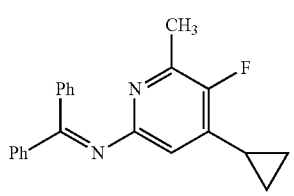

(c) reacting the compound of formula 2a with hydrochloric acid in one or more solvents to obtain the compound of formula 5; and

5

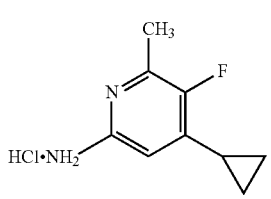

(d) obtaining the compound of formula 5 as crystalline monohydrate by crystallizing the compound of formula 5 in one or more solvents.

8. The process according to claim 7, wherein steps (a)-(c) are performed in a single solvent in one-pot.

9. The crystalline triaminopyrimidine compound of formula 1 according to claim 1, having a purity of about 99% or more and total impurities of about 1.0% or less, by weight as measured by area percentage by HPLC.

10. The crystalline triaminopyrimidine compound of formula 1 according to claim 9, which is substantially free from one or more of the compounds selected from the group consisting of a compound of formula 11, a compound of formula 12, a compound of formula 13, a compound of formula 14 and a compound of formula 15, wherein the formulas of these compounds are:

11

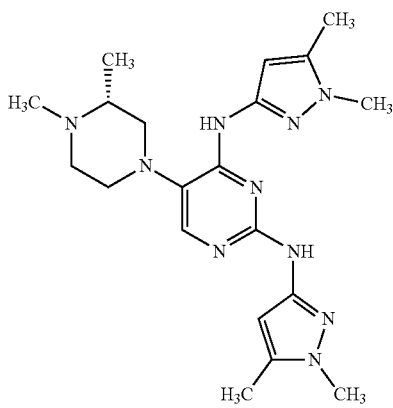

12

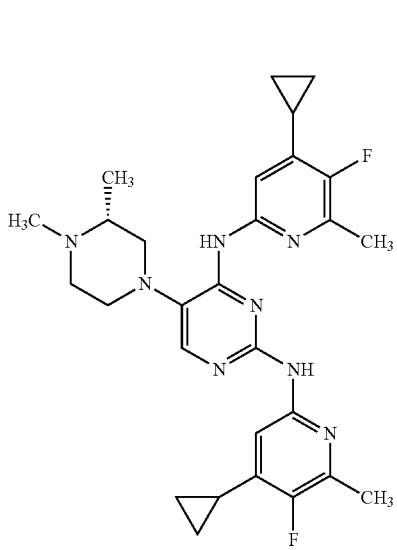

13

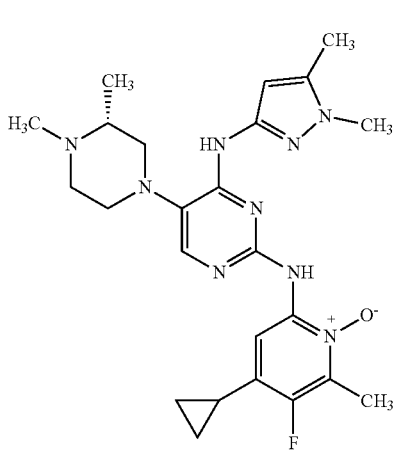

-continued

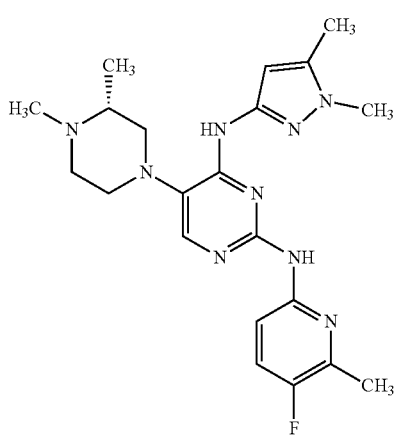

14

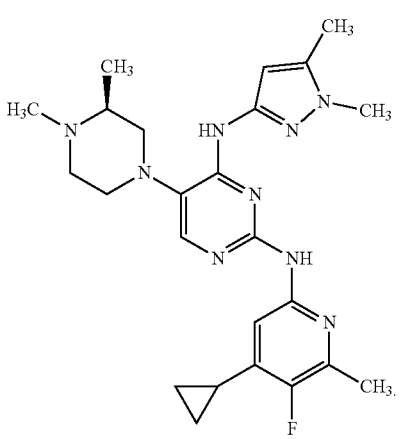

15

11. A composition comprising the crystalline triaminopyrimidine compound of formula 1 according to claim 1, wherein the triaminopyrimidine compound of formula 1 has a purity of about 99% or more by weight, and (S)-$N^2$-(4-cyclopropyl-5-fluoro-6-methylpyridin-2-yl)-$N^4$-(1,5-dimethyl-1H-pyrazol-3-yl)-5-(3,4-dimethyl-piperazine-1-yl) pyrimidine-2,4-diamine (relative to the triaminopyrimidine compound of formula 1) is present in an amount of about 0.5% or less, by weight as measured by area percentage of HPLC.

12. A composition comprising the crystalline triaminopyrimidine compound of formula 1 according to claim 1, wherein the triaminopyrimidine compound of formula 1 has a purity of about 99% or more by weight, and (R)-4-cyclopropyl-6-((4-((1,5-dimethyl-1H-pyrazol-3-yl) amino)-5-(3,4-dimethylpiperazin-1-yl) pyrimidin-2-yl) amino)-3-fluoro-2-methylpyridine-1-oxide (relative to the triaminopyrimidine compound of formula 1) is present in an amount of about 0.5% or less, by weight as measured by area percentage of HPLC.

13. A process for the preparation of the crystalline triaminopyrimidine compound of formula 1 according to claim 1, the process comprising:

(a) reacting a compound of formula 10 with a compound of formula 9 in one or more solvents to obtain a compound of formula 8;

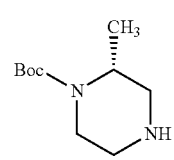

10

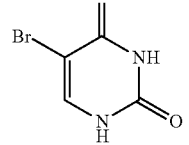

9

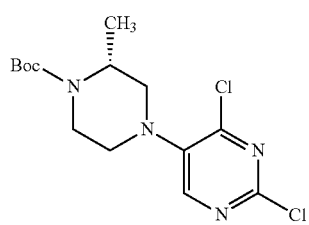

8

(b) reacting the compound of formula 8 with a chlorinating agent in one or more solvents to obtain a compound of formula 7;

7

(c) reacting the compound of formula 7 with a compound of formula 6 in one or more solvents in the presence of a first base to obtain a compound of formula 4;

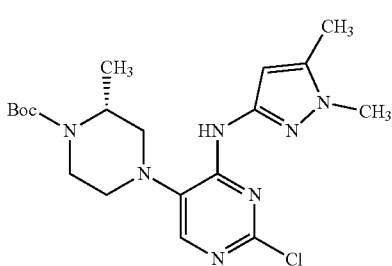

6

4

(d) reacting the compound of formula 4 with a compound of formula 5 or a hydrate thereof in one or more solvents in the presence of a second base to obtain a compound of formula 3 or solution thereof;

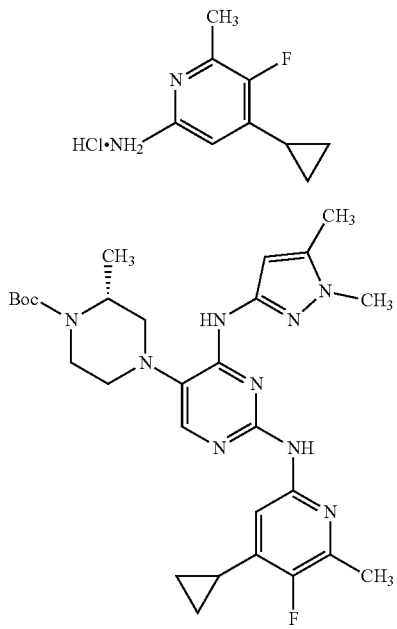

5

3

(e) reacting the compound of formula 3 or solution thereof with an acid in one or more solvents to obtain a compound of formula 2, which is a free base;

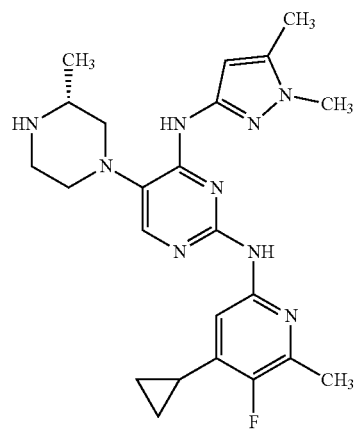

2

(f) reacting the compound of formula 2 with a methylating agent in one or more solvents to obtain the compound of formula 1; and
(g) crystallizing the compound of formula 1 in one or more solvents.

14. The process according to claim 13, wherein the chlorinating agent at step (b) is selected from phosphorus oxychloride, phosphorus pentachloride, phosphorus trichloride, and thionyl chloride.

15. The process according to claim 13, wherein the first or second base at step c or d comprises one or more bases selected from sodium hydroxide, potassium hydroxide, lithium hydroxide, barium hydroxide, sodium carbonate, potassium carbonate, barium carbonate, cesium carbonate, sodium bicarbonate, potassium bicarbonate, pyridine, piperidine, morpholine, TEA, DIPEA, DBU, STB, PTB, or DABCO.

16. The process according to claim 13, wherein the acid comprises one or more acids selected from hydrochloric acid, hydrobromic acid, acetic acid, phosphoric acid, and trifluroacetic acid.

17. The process according to claim 13, wherein the solvent at step (e) comprises one or more solvents selected from methanol, ethanol, isopropanol, butanol, acetone, methyl ethyl ketone, methyl isobutyl ketone, isopropyl acetate, butyl acetate, dimethylformamide, dimethylacetamide, dimethylsulfoxide, acetonitrile and water, or mixtures thereof.

18. A process for crystallizing a free base compound of formula 2,

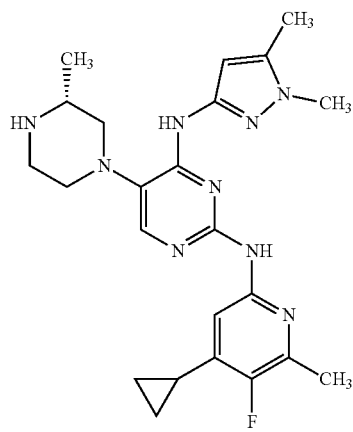

2 the process comprising crystallizing the free base compound of formula 2 from one or more solvents selected from methanol, ethanol, isopropanol, butanol, acetone, methyl ethyl ketone, methyl isobutyl ketone, isopropyl acetate, butyl acetate, dimethylformamide, dimethylacetamide, dimethylsulfoxide, acetonitrile, water, or mixtures thereof.

19. A process for the preparation of the crystalline triaminopyrimidine compound of formula 1 according to claim 1, the process comprising methylating a free base compound of formula 2

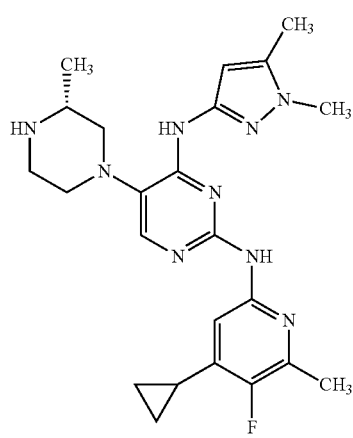

2 with a methylating agent, optionally in the presence of a reducing agent, in one or more solvents.

20. The process according to claim 19, wherein the methylating agent comprises one or more of diazomethane, dimethyl carbonate, dimethyl sulfide, methyl fluorosulfonate, methyl iodide, methyl bromide, methyltrifluoro methane sulfonate, trimethoxonium tetraflouroborate, formaldehyde, and mixture of formic acid and formaldehyde.

21. The process according to claim 19, wherein the reducing agent comprises one or more agents selected from sodium cyanoborohydride, sodium triacetoxyborohydride, lithium aluminium hydride, and sodium borohydride.

22. A process for the preparation of the crystalline triaminopyrimidine compound of formula 1 according to claim 1, the process comprising crystallizing the triaminopyrimidine compound of formula 1 in one or more solvents selected from methanol, ethanol, isopropanol, butanol, acetone, methyl ethyl ketone, methyl isobutyl ketone, isopropyl acetate, butyl acetate, dimethylformamide, dimethylacetamide, dimethylsulfoxide, acetonitrile, water, or mixtures thereof.

23. A pharmaceutical composition comprising the crystalline triaminopyrimidine compound of formula 1 according to claim 1, and pharmaceutically acceptable carrier, diluents and excipients.

24. A pharmaceutical composition comprising the crystalline triaminopyrimidine compound of formula 1 according to claim 9, and one or more of pharmaceutically acceptable carriers, diluents and excipients.

25. A method of treatment of malaria comprising administering to a subject in need thereof a pharmaceutical composition comprising the crystalline triaminopyrimidine compound of formula 1 according to claim 1.

* * * * *